(12) United States Patent
Chorny et al.

(10) Patent No.: US 11,253,603 B2
(45) Date of Patent: Feb. 22, 2022

(54) POLYMER-BASED MACROMOLECULAR PRODRUGS

(71) Applicant: The Children's Hospital of Philadelphia, Philadelphia, PA (US)

(72) Inventors: Michael Chorny, Huntington Valley, PA (US); Ivan Alferiev, Clementon, NJ (US); Garrett M. Brodeur, Wynnewood, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 16/969,790

(22) PCT Filed: Sep. 17, 2019

(86) PCT No.: PCT/US2019/051457
§ 371 (c)(1),
(2) Date: Aug. 13, 2020

(87) PCT Pub. No.: WO2020/061007
PCT Pub. Date: Mar. 26, 2020

(65) Prior Publication Data
US 2021/0000967 A1 Jan. 7, 2021

Related U.S. Application Data

(60) Provisional application No. 62/732,199, filed on Sep. 17, 2018.

(51) Int. Cl.
*A61K 47/60* (2017.01)
*A61K 31/4745* (2006.01)

(52) U.S. Cl.
CPC .......... *A61K 47/60* (2017.08); *A61K 31/4745* (2013.01)

(58) Field of Classification Search
CPC .. A61K 47/60; A61K 31/4745; A61K 31/167; A61K 45/06; A61P 31/00
See application file for complete search history.

(56) References Cited

U.S. PATENT DOCUMENTS

| | | |
|---|---|---|
| 7,744,861 B2 | 6/2010 | Zhao et al. |
| 8,263,062 B2 | 9/2012 | Zhao et al. |
| 8,318,145 B2 | 11/2012 | Zhao et al. |
| 8,394,365 B2 | 3/2013 | Zhao et al. |
| 8,617,558 B2 | 12/2013 | Govindan et al. |
| 8,771,662 B2 | 7/2014 | Zhao et al. |
| 8,906,353 B2 | 12/2014 | Eldon et al. |
| 9,226,969 B2 | 1/2016 | Chong et al. |
| 9,320,808 B2 | 4/2016 | Chong et al. |
| 9,333,200 B2 | 5/2016 | Zhao et al. |
| 9,801,873 B2 | 10/2017 | Eldon et al. |
| 9,808,533 B2 | 11/2017 | Zhao et al. |
| 9,863,949 B2 | 1/2018 | Hoch et al. |
| 10,132,810 B2 | 11/2018 | Chia et al. |
| 10,413,547 B2 | 9/2019 | Strum et al. |
| 10,434,182 B2 | 10/2019 | Weng et al. |
| 10,463,659 B2 | 11/2019 | Zhao et al. |
| 10,525,051 B2 | 1/2020 | Eldon et al. |
| 10,660,969 B2 | 5/2020 | Weng et al. |
| 10,758,614 B2 | 9/2020 | Saha et al. |
| 10,869,863 B2 | 12/2020 | Yuan et al. |
| 2005/0112088 A1 | 5/2005 | Zhao et al. |
| 2007/0254019 A1* | 11/2007 | Zamboni ............... A61K 9/0019 424/450 |
| 2008/0194612 A1 | 8/2008 | Zhao et al. |
| 2009/0074074 A1 | 3/2009 | Au et al. |
| 2010/0152414 A1 | 6/2010 | Zhao et al. |
| 2010/0190933 A1 | 7/2010 | Zhao et al. |
| 2011/0269789 A1 | 11/2011 | Eldon et al. |
| 2012/0171201 A1 | 7/2012 | Sapra |
| 2013/0143909 A1 | 6/2013 | Chong et al. |
| 2013/0158062 A1 | 6/2013 | Zhao et al. |
| 2013/0231359 A1 | 9/2013 | Chong et al. |
| 2014/0323514 A1 | 10/2014 | Zhao et al. |
| 2014/0357659 A1 | 12/2014 | Hoch et al. |
| 2014/0371258 A1 | 12/2014 | Gu et al. |
| 2015/0087668 A1 | 3/2015 | Eldon et al. |
| 2015/0105519 A1 | 4/2015 | Chong et al. |
| 2015/0309032 A1 | 10/2015 | Chia et al. |
| 2016/0144045 A1* | 5/2016 | Kozlowski ........... A61K 31/785 546/48 |
| 2016/0200867 A1 | 7/2016 | Kozlowski et al. |
| 2017/0056514 A1 | 3/2017 | Zhao et al. |
| 2017/0112928 A1 | 4/2017 | Saha et al. |
| 2017/0246171 A1 | 8/2017 | Strum et al. |

(Continued)

FOREIGN PATENT DOCUMENTS

| | | | |
|---|---|---|---|
| CN | 101385860 A * | 3/2009 | ............. A61K 47/48 |
| CN | 101385860 A | 3/2009 | |

(Continued)

OTHER PUBLICATIONS

International Search Report and itten Opinion for International Application No. PCT/US2019/051457, dated Nov. 19, 2019, 9 pages.

Ulbrich et al., "Targeted Drug Delivery with Polymers and Magnetic Nanoparticles: Covalent and Noncovalent Approaches, Release Control, and Clinical Studies", Chemical Reviews, vol. 116, Apr. 25, 2016, pp. 5338-5377.

Ekladious et al., "Polymer-Drug Conjugate Therapeutics: Advances, Insights and Prospects", Nature Reviews, 2019, 22 pages.

Fontaine et al., "PLX038: A PEGylated Prodrug of SN-38 Independent of UGT1A1 Activity", Cancer Chemotherapy and Pharmacology, 2020, vol. 85, pp. 225-229. 5 pages.

Fontaine et al., "PLX038: A PEGylated Prodrug of SN-38 Independent of UGT1A1 Activity", Cancer Chemotherapy and Pharmacology, Supporting Information, 2020. 4 pages.

(Continued)

*Primary Examiner* — Phuong Huynh
(74) *Attorney, Agent, or Firm* — RatnerPrestia

(57) ABSTRACT

Provided are macromolecular prodrugs in which camptothecin analogs are covalently bonded to polymers via ester bonds that are labile under physiological conditions. Also provided are methods of treating cancer, especially neuroblastoma with the macromolecular prodrugs.

7 Claims, 13 Drawing Sheets

(56) References Cited

U.S. PATENT DOCUMENTS

| | | |
|---|---|---|
| 2017/0312363 A1 | 11/2017 | Weng et al. |
| 2018/0021444 A1 | 1/2018 | Zhao et al. |
| 2018/0028525 A1 | 2/2018 | Eldon et al. |
| 2018/0095085 A1 | 4/2018 | Hoch et al. |
| 2018/0214561 A1 | 8/2018 | Weng et al. |
| 2019/0030034 A1 | 1/2019 | Strum et al. |
| 2019/0049450 A1 | 2/2019 | Chia et al. |
| 2019/0365910 A1 | 12/2019 | Weng et al. |
| 2019/0375732 A1 | 12/2019 | Hung et al. |
| 2020/0000797 A1 | 1/2020 | Yuan et al. |
| 2020/0016149 A1 | 1/2020 | Zhao et al. |
| 2020/0022983 A1 | 1/2020 | Strum et al. |
| 2020/0163956 A1 | 5/2020 | Abrams et al. |
| 2020/0360523 A1 | 11/2020 | Hung et al. |
| 2021/0000967 A1 | 1/2021 | Chorny et al. |
| 2021/0008218 A1 | 1/2021 | Yuan et al. |
| 2021/0024693 A1 | 1/2021 | Kozlowski et al. |
| 2021/0121434 A1 | 4/2021 | Ames et al. |

FOREIGN PATENT DOCUMENTS

| | | |
|---|---|---|
| EP | 2626083 A1 | 8/2013 |
| WO | 9952861 A1 | 10/1999 |
| WO | 2005028539 A2 | 3/2005 |
| WO | 2019090141 A1 | 5/2019 |
| WO | 2020169004 A1 | 8/2020 |

OTHER PUBLICATIONS

Hoch et al., "Nonclinical Pharmacokinetics and Activity of Etirinotecan Pegol (NKTR-102) a Long-Acting Topoisomerase 1 Inhibitor, in Multiple Cancer Models", Cancer Chemotherapy Pharmacology, 2014, vol. 74, pp. 1125-1137.

Santi et al., "Macromolecular Prodrug That Provides The Irinotecan (CPT-11) Active-Metabolite SN-38 with Ultralong Half-Life, Low Cmax, and Low Glucuronide Formation", Journal of Medicinal Chemistry, 2014, vol. 57, pp. 2303-2314.

Sapra et al., "Novel Delivery of SN38 Markedly Inhibits Tumor Growth in Xenografts, Including a Camptothecin-11-Refractory Model", Clinical Cancer Research, 2008, vol. 14, pp. 1888-1896.

International Preliminary Report on Patentability and Written Opinion for International Application No. PCT/US2019/051457, dated Mar. 9, 2021, 8 pages.

* cited by examiner

A

B

POLYMER-BASED MACROMOLECULAR PRODRUGS

CROSS-REFERENCE TO RELATED APPLICATIONS

This application is the national phase of International Application No. PCT/US2019/051457, filed 17 Sep. 2019, which claims priority to U.S. Provisional Application No. 62/732,199, filed 17 Sep. 2018. The disclosure of each of these applications is incorporated herein by reference in its entirety for all purposes.

FIELD

Provided are macromolecular prodrugs in which camptothecin analogs are covalently bonded to polymers via ester bonds that are labile under physiological conditions. Also provided are methods of treating cancer, in particular neuroblastoma, with the macromolecular prodrugs.

BACKGROUND

Neuroblastoma (NB) remains the most common and deadly solid tumor of childhood accounting for 8-10% of alt childhood cancers, and 15% of deaths from cancer in children. Despite improvements in the cure rate for other pediatric neoplasms, the survival rate for patients with NB has lagged behind.

The intensive, multimodality therapy currently used in the clinic fails in over half of the patients (50-60% of patients experience a relapse with no curative salvage treatment options), with the most formidable therapeutic challenge presented by the non-responder patient subgroup, defined as an "ultrahigh" risk category. High-risk NB with its highly diverse etiology and prevalence of biologically unfavorable variants is currently approached by potent anticancer agents as a first-line treatment, including topoisomerase I inhibitors of the camptothecin family: topotecan and irinotecan. However, their clinical use in the context of aggressive disease remains suboptimal, yielding poor results in relapsed or refractory NB patients due to dose-limiting side effects and acquired drug resistance. Importantly, treatment failure in these patients was shown to be associated with an increase in threshold drug levels required for effectively suppressing NB cell growth by 1-3 orders of magnitude, reaching values not achievable clinically.

Thus, to combat refractory NB there is a need for alternative therapeutic approaches, which can markedly enhance intratumoral delivery and extend drug presence at therapeutically effective drug levels without increasing systemic exposure. The embodiments described herein address this need.

SUMMARY

In a first embodiment, a macromolecular prodrug is provided in which at least two molecules of a camptothecin analog are covalently bonded to a poloxamer polymer via ester bonds that are labile under physiological conditions (e.g., 22° C., pH=7.2).

In a second embodiment, a macromolecular prodrug is provided in which at least two molecules of an SN22 analog are covalently bonded to a PEG polymer via ester bonds that are labile under physiological conditions.

In a third embodiment, a macromolecular prodrug is provided in which at least two molecules of a camptothecin analog are covalently bonded to a polymer via ester bonds that are labile under physiological conditions, wherein at least one camptothecin analog is functionalized with at least one NE transporter (NET) ligand.

In another embodiment, the camptothecin analog is SN22 (7-ethyl-camptothecin), SN38 (7-ethyl-10-hydroxy-camptothecin) or a combination thereof.

In another embodiment, the polymer is a poloxamer polymer.

In another embodiment, the polymer is a polyethylene glycol (PEG) polymer.

In another embodiment, the polymer is a multi-arm PEG polymer.

In another embodiment, two molecules of the camptothecin analog are covalently bonded to the polymer.

In another embodiment, four molecules of the camptothecin analog are covalently bonded to the polymer.

In another embodiment, two to eight molecules of the camptothecin analog are covalently bonded to the polymer.

In another embodiment, the NE transporter (NET) ligand is covalently bonded to the camptothecin analog via an ester bond that is labile under physiological conditions.

In another embodiment, the camptothecin analog is SN-38.

In another embodiment, the NE transporter (NET) ligand is benzylguanidine (BG).

In another embodiment, the NE transporter (NET) ligand is phenethylguanidine or tyramine.

In another embodiment, the ester bond between the NE transporter (NET) and the camptothecin analog is a oxyhexanoyl ester.

In another embodiment, the ester bond between the NE transporter (NET) ligand and the camptothecin analog is an oxyethoxypropanoyl or oxethoxyethoxypropanoyl ester.

In another embodiment, the macromolcular prodrug is [PEG-SN38-BG]$_8$.

In another embodiment, the macromolcular prodrug is PF108-(SN22)$_2$.

In another embodiment, the macromolcular prodrug is PEG-[SN22]$_4$.

In another embodiment, the ester bonds are oxyacetate ester bonds.

In another embodiment a method of treating neuroblastoma is provided, by administering an effective amount of the macromolcular prodrug as defined above to a subject in need thereof.

In another embodiment, a method of treating a subject with a solid tumor is provided, by administering an effective amount of the macromolecular prodrug as defined above to a subject in need thereof.

In another embodiment, a method of treating a subject with a brain tumor is provided, by administering an effective amount of the macromolecular prodrug as defined above to a subject in need thereof.

In another embodiment, a method of treating cancer is provided, by administering an effective amount of the macromolecular prodrug as defined above to a subject in need thereof.

In another embodiment, the subject in need thereof is a human.

DETAILED DESCRIPTION

First Embodiment

Figure 1:
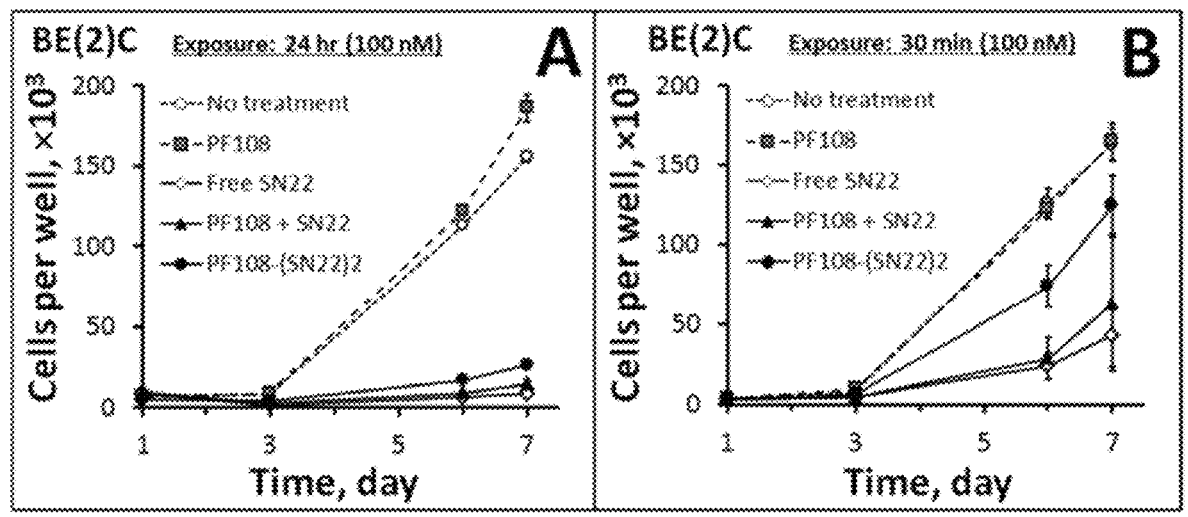
FIG. 1: Growth inhibition of chemoresistant NB cells [BE(2)C] by PF108-(SN22)$_2$ prodrug vs. SN22 with or without Pluronic F-108 (doses equivalent to 100 nM SN22). Cells untreated or treated with plain, chemically unmodified Pluronic F-108 were included as controls. Tested exposure durations included 24 hours and 30 minutes (A and B, respectively). Cell growth was monitored over time by bioluminescence. Results are shown as mean±SD.

In the first embodiment of the prodrug described above, at least two molecules of a camptothecin analog are covalently bonded to a poloxamer polymer via ester bonds that are labile under physiological conditions (e.g. 22° C., pH=7.2).

Camptothecin analogs are well-known in the art as topoisomerase inhibitors. Camptothecin itself is (S)-4-ethyl-4-hydroxy-1H-pyrano[3',4':6,7]indolizino[1,2-b]-quinoline-3, 14-(4H,12H)-dione. The term "camptothecin analog" includes camptothecin. Preferred camptothecin analogs include SN22 (7-ethyl-camptothecin), SN38 (7-ethyl-10-hydroxy-camptothecin), or a combination thereof.

Poloxamers are nonionic triblock copolymers composed of a central hydrophobic chain of polyoxypropylene (poly (propylene oxide)) flanked by two hydrophilic chains of polyoxyethylene (poly(ethylene oxide)). The total number of chains of polyoxyethylene may range from 2 to 130. The number of oxypropylene units may range from 15-67. Preferably, the molecular weight of the Poloxamer is below the threshold a glomerular filtration (30-50 kDa). These polymers have a history of safe use in humans and are available as pharmaceutical grade materials (Kolliphor® P). A number of Poloxamer have been approved by FDA as excipients and are currently in clinical use for a variety of applications. All of these Poloxamers are suitable for the embodiments described herein.

The biologically relevant properties of Poloxamers, such as molecular size and hydrophilic/lipophilic balance, are controlled through adjusting the lengths of the hydrophilic (A) and hydrophobic (B) blocks [A=poly(ethylene oxide) (PEO) and B=poly(propylene oxide) (PPO)], and their molar ratio. Unlike chemically homogeneous poly(ethylene oxides), the ABA triblock Poloxamers combining intermediate lengths of the middle PPO blocks with comparatively high hydrophylic/lipophilic balance values are capable of stably associating with cell membranes, which provides an effective mechanism for tumor penetration and for extending intratumoral presence. Examples of Poloxamers include Kolliphor® P188, P338 and P407.

The camptothecin analogs are covalently bonded to a poloxamer polymer via ester bonds that are labile under physiological conditions (e.g. 22° C., pH=7.2). In one embodiment, the ester bonds are oxyacetate ester bonds. The camptothecin analogs are preferably bonded to the poloxamer polymer via a hydroxyl group at the position corresponding to position 20 in camptothecin.

In another embodiment, two molecules the camptothecin analog are covalently bonded to the Poloxamer polymer. In a preferred embodiment, the macromoleculer prodrug is PF108-(SN22)$_2$, which is represented by the following structure:

polymers may have a molecular weight of 1,000 to 100,000 daltons, inclusive of all values and subranges therebetween including 2,000, 5,000, 10,000, 25,000, 35,000, 50,000, 75,000 and 85,000 daltons.

In another embodiment, two molecules of SN22 are covalently bonded to a linear PEG polymer. In another embodiment, four molecules of SN22 are covalently bonded to a multi-arm PEG polymer having four PEG chains. In another embodiment, more than four and up to eight molecules of SN22 are covalently bonded to a multi-arm PEG polymer. Preferably, a molecule of SN22 is covalently bonded to each of the PEG chains in these embodiments.

The SN22 moieties are covalently bonded to a PEG polymer via ester bonds that are labile under physiological conditions (e.g., 22° C., pH=7.2). In one embodiment, the ester bonds are oxyacetate ester bonds. The camptothecin analogs are preferably bonded the PEG polymer via a hydroxy group at the position corresponding to position 20 in camptothecin.

In a preferred embodiment, the macromolecular prodrug is PEG-[SN22]$_4$, which is represented by the following structure:

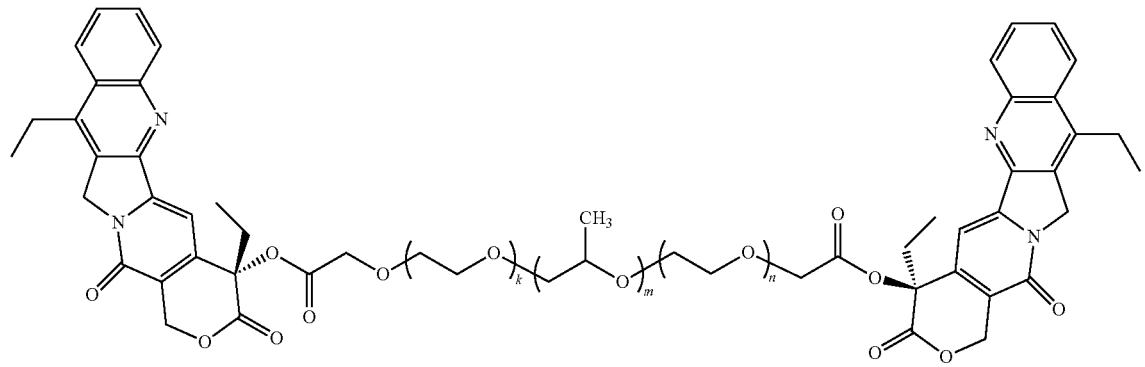

k + n ≅ 270; m ≅ 44

Second Embodiment

In the second embodiment of the prodrug described above, at least two molecules of an SN22 analog are covalently bonded to a PEG polymer via ester that are labile under physiological conditions.

Polyethylene glycol (PEG) polymers are well-known in the art. PEG polymers may be linear and represented by the formula H—(O—CH$_2$—CH$_2$)$_n$—OH. In another embodiment, the PEG polymer is a multi-arm polymer. Multi-arm PEG polymers have three to ten PEG chains emanating from a central core group. Four PEG chain are particularly preferred. Preferred central core groups include a pentaerythritol group and a tripentaerythritol group. The PEG

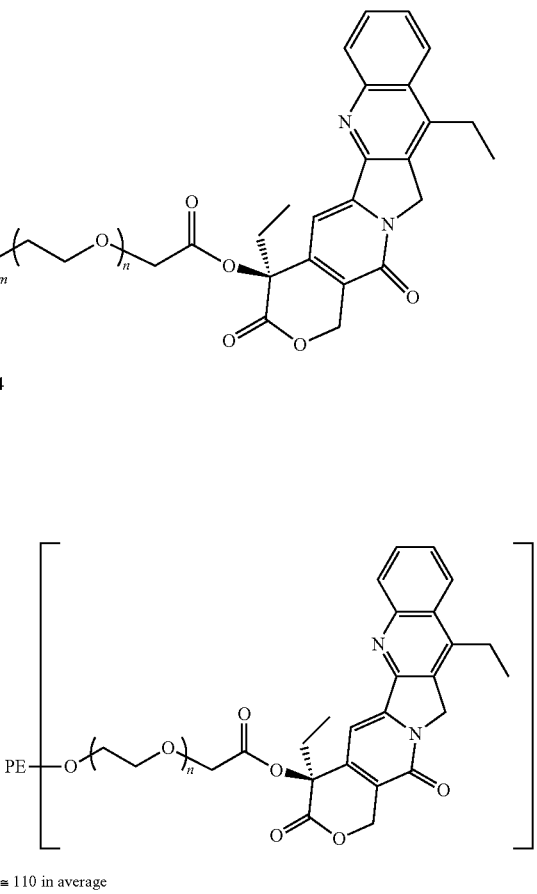

n ≅ 110 in average

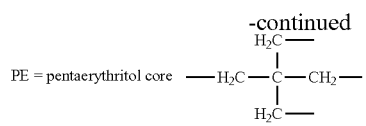

In another embodiment, the patient can be pre-treated with Temozolomide (TMZ), which is an oral chemotherapy drug. Such pretreatment army provide additive efficacy, but may will enhance tumor penetration of the prodrug. Temozolomide can administered at a dose of 20 to 250 mg/kg/day PO for several days, e.g., 5 days followed by prodrug treatment, e.g., beginning on day 7. A dose of 100 mg/kg/day PO is preferred.

Third Embodiment

In the third embodiment of the prodrug described above, at least two molecules of a camptothecin analog are covalently bonded to a polymer via ester bonds that are labile under physiological conditions, wherein at least one camptothecin analog is functionalized with at least one NE transporter (NET) ligand.

The camptothecin analog may be SN22 (7-ethyl-camptothecin), SN38 (7-ethyl-10-hydroxy-camptothecin) or a combination thereof. SN38 is particularly preferred.

In another embodiment, two to eight molecules of the camptothecin analog are covalently bonded to the polymer. This range includes all specific values and subranges therebetween, such as two, three, four, five, six and seven molecules of the camptothecin analog. Eight molecules of the camptothecin analog covalently bonded to the polymer is particularly preferred.

The polymer may be a poloxamer polymer or a PEG polymer, such as described above. A multi-arm PEG polymer is preferred. In this embodiment, a multi-arm PEG polymers have three to ten PEG chains emanating from a central core group. Four to eight PEG chains are particularly preferred, with eight PEG chains particularly preferred. Preferred central core groups include a pentaerythritol group and a tripentaerythritol group. A tripentaerythritol group is particularly preferred as a central core group.

The camptothecin analogs are covalently bonded to a poloxamer polymer via ester bonds that are labile under physiological conditions (e.g., 22° C., pH=7.2). In one embodiment, the ester bonds are oxyacetate ester bonds. The camptothecin analogs are preferably bonded to the poloxamer polymer via a hydroxyl group at the position corresponding to position 20 in camptothecin.

In this embodiment, at least one camptothecin analog is functionalized with at least one ligand for the norepinephrine (NE) transporter, i.e., a NE transporter (NET) ligand. In one embodiment, the NE transporter (NET) ligand is phenethylguanidine, benzylguanidine (BG) or tyramine. Benzylguanidine is particularly preferred.

In another embodiment, the NE transporter (NET) ligand is covalently bonded to the camptothecin analog via an ester bond that is labile under physiological conditions. In a preferred embodiment, the ester bond between the NE transporter (NET) ligand and the camptothecin analog is an oxyhexanoyl ester. In another embodiment, the ester bond between the NE transporter (NET) ligand and the camptothecin analog is an oxyethoxypropanoyl oxyethoxyethoxypropanoyl ester.

In a preferred embodiment, the macromolecular prodrug is [PEG-SN38-BG]$_8$, which is represented by the following structure:

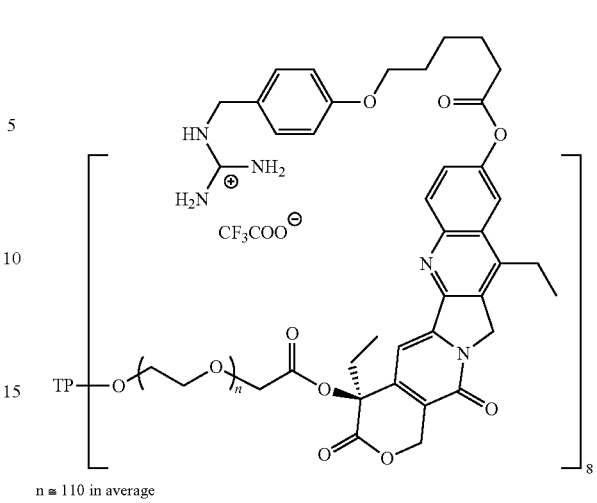

n ≈ 110 in average

TP = tripentaerythritol core

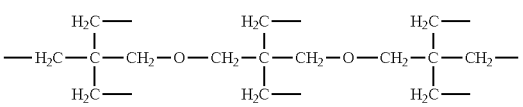

Methods of Treatment

As described above, the macromolecular prodrug can be used in a method of treating neuroblastoma by administering an effective amount of the macromolecular prodrug to a subject in need thereof.

The macromolecular prodrug as described above can also be used in a method of treating a subject with a solid tumor by administering an effective amount of the macromolecular prodrug to a subject in need thereof.

The macromolecular prodrug as described above can also be used in a method of treating a subject with a brain tumor by administering an effective amount of the macromolecular prodrug to a subject in need thereof.

The macromolecular prodrug as described above can also be used in a method of treating cancer by administering an effective amount of the macromolecular prodrug as defined above to a subject in need thereof.

In these embodiments, the subject in need thereof is preferably a mammal, with humans especially preferred.

The macromolecular prodrug may be administered by any method commonly used in the art. Methods of administration Include parenteral (intravenous, intramuscular, and subcutaneous), oral, nasal, ocular, transmucosal (buccal, vaginal, and rectal), and transdermal routes of administration.

The macromolecular prodrug may be administered at any dose effective to treat the conditions described herein. The dosage of the macromolecular prodrug may be from 0.5 to 200 mg/kg per dose.

EXAMPLES

Example 1: PF108-(SN22)$_2$

1. Two-Step Prodrug Synthesis.

Oxidation of Poloxamers with Jones reagent (CrO$_3$/H$_2$SO$_4$) in THF at 22-25° C. transforms polymers' terminal CH$_2$OH into terminal alkoxyacetate carboxylic groups, which then can be used for reversible covalent binding of various hydroxyl-containing drugs via hydrolysable ester bonds. Oxidation of Pluronic F-108 (Kolliphor P338) in the conditions mentioned above resulted in a polymer containing 0.18 mmol/g of carboxylic groups, as was determined using $^1$H NMR by the signal of $OCH_2CO$ protons. Analogously, oxidation of Pluronic F-68 resulted in a polymer containing 0.23 mmol/g of terminal carboxylic groups. Further conjugation of the carboxylated Pluronic F-108 with SN22 using 1,3-dicyclohexylcarbodiimide (DCC) as an activating agent for the carboxylic groups, 4-dimethylaminopyridine tosylate (DPTS) as a catalyst and $CH_2Cl_2$ as a solvent formed a polymeric conjugate containing 0.13 mmol/g or 4.8% wt. of the drug. $^1$H NMR demonstrated that SN-22 was covalently bound to the polymer via ester bonds between the carboxylic groups of the carboxylated Pluronic and 20-OH of the SN22 molecule. Kolliphor-grade Pluronics (Table 1) and SN22 (purity: ≥97%, HPLC) will be purchased from Sigma-Aldrich (St. Louis, Mo.) and AK Scientific (Union City, Calif.), respectively.

To prepare prodrugs of SN38 with carboxylated Pluronics, the phenolic 10-OH of SN38 (purity: ≥97%, AstaTech, Bristol, Pa.) is first protected with 10-tert-butyldiphenylsilyl (TBDPS) group by action of tert-butyl(chloro)diphenylsilane (TBDPS-Cl) in the presence of imidazole in N-methylpyrrolidone. In a feasibility experiment, the resulting 10-TBDPS-protected SN38 (obtained in a 97% yield) was reacted as above with carboxylated Pluronic F-68, yielding after the following deprotection (with pyridinium fluoride in $CH_2Cl_2$) the aim conjugate, which according to $^1$H NMR contained 0.17 mmol/g or 6.6% wt. of SN38 covalently bound via ester bonds by the 20-OH.

TABLE 1

Pharmaceutical-grade Poloxamer polymers used to make prodrug conjugates described herein.

| Poloxamer | Ethylene oxide units | Propylene oxide units | Molecular weight | HLB value |
|---|---|---|---|---|
| Kolliphor | 150-170 | 25-40 | 7680-9510 | >24 |
| Kolliphor | 274-292 | 42-51 | 12700-17400 | >24 |
| Kolliphor | 190-210 | 54-60 | 9840-14600 | 18-23 |

2. Poloxamer-SN22 Prodrug Inhibits Growth of NB Cells.

Refractory NB is characterized by a shift in threshold drug levels required for inhibiting NB cell growth. This shift shown is all tested cell line pairs, derived from same patients with progressive disease during induction therapy vs. at diagnosis before therapy, simultaneously affects response to chemotherapeutic agents from different chemical and pharmacological families. PF108-(SN22)$_2$, a prodrug constructed from pharmaceutical-grade Pluronic F-108 (Kolliphor P338) and SN22, was tested against a BE(2)C cell line exhibiting a drug-resistant phenotype associated with acquisition of a TP53 mutation on codon 135 and the loss of p53 function.

After a 24-hr exposure, PF108-(SN22)$_2$ effectively inhibited growth of BE(2)C cells over 7 days, with potency similar to that of SN22 alone or in combination with chemically unmodified Pluronic F-108 (PF108+SN22), whereas no cell growth inhibition was observed with Pluronic F-108 applied without drug (FIG. 1A). The effect of PF108-(SN22)$_2$ was markedly less pronounced when the exposure was limited to 30 min (FIG. 1B), suggesting that the prodrug largely remains intact on this time scale.

Figure 4:
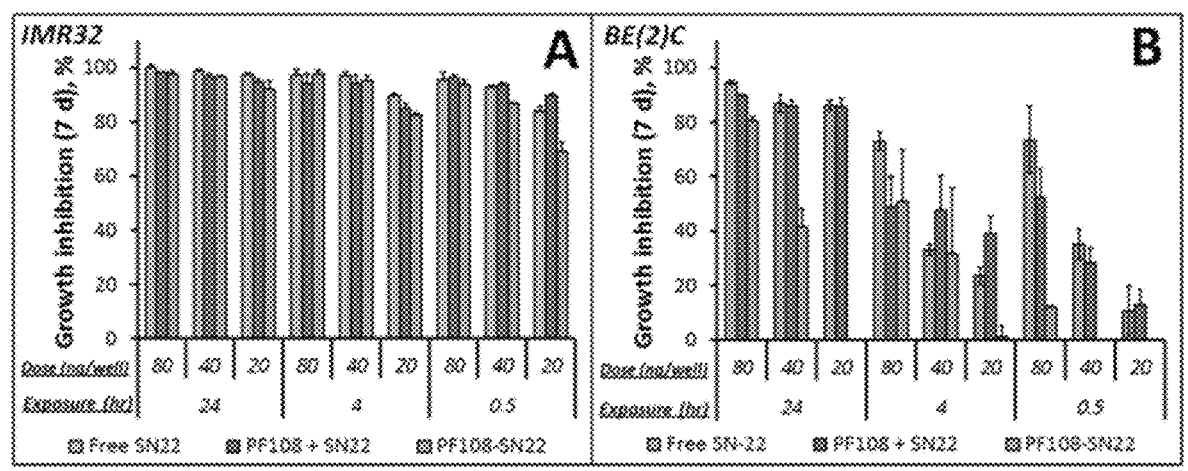
FIG. 4: Testing antiproliferative effect of PF108-(SN22)$_2$ prodrug vs. free SN22 with/without blank Pluronic F-108. The response to treatment was compared between NB cells exhibiting chemo-naïve vs. chemoresistant phenotypes (IMR32 (A) and BE(2)C (B), respectively) as a function of exposure duration (0.5, 4 and 24 hr) and dose (equivalent to 20, 40 and 80 ng SN22 per well). The response is shown as % growth inhibition (mean±SD) at 7 days post-treatment.

In comparison, when tested against chemo-naïve NB cells (IMR-32), the prodrug was uniformly effective within the dose range corresponding to 20-80 nM of SN22 and exposure durations from 30 min to 24 hr, causing profound IMR-32 cell growth inhibition (See FIG. 4A). This is consistent with a lack or intrinsic resistance in this cell line derived from a previously untreated patient, making it responsive to the antiproliferetive effect of active SN22 present at substantially lower. Importantly, while free SN22 was included as a positive control in cell culture experiments, it is incompatible with pharmaceutically acceptable vehicles.

3. SN22 Delivery as a Poloxamer Prodrug Achieves Extended Exposure in Orthotopic BE(2)C Tumors.

A comparison between BE(2)C cells derived at relapse after chemo-radiotherapy and BE(1) cells derived from the same patient at diagnosis demonstrated an order of magnitude increase in the concentration of a camptothecin analog, SN38, required for achieving cell growth inhibition by 90%: 25 vs, 2 ng/ml, respectively. Importantly, it was shown that the corresponding intratumoral level of SN38 cannot be maintained using conventional treatment with its precursor, irinotecan (CPT-11). The inability to keep effective local drug levels without exceeding the maximal tolerated dose is the main cause for the failure of clinically used camptothecins and other chemotherapeutics in the settings of recurrent and refractory, high-risk NB. In agreement with these reports, these results show less than 25 ng/g and 2 ng/g of SN38 in large (≥1 cm$^3$) BE(2)C orthotopic xenografts at 24 and 72 hr, respectively, after administration of irinotecan (10 mg/kg). In comparison, SN22 delivered at an, equivalent dose as PF108-(SN22)$_2$ was stably present in the tumors at many fold higher levels: 2180±850 ng/g, 2140±520 ng/g, and 1570±580 ng/g, at 4, 24 and 72 hr, respectively (FIG. 2), suggesting that Poloxamer prodrug-based delivery can maintain stable therapeutically effective levels of SN22, thus addressing the prerequisite for a lasting NB tumor growth suppression.

4. Paloxamer-SN22 Prodrug Potently Tumor Growth Prolonging Survival in Drug-Resistant NB.

Figure 3:
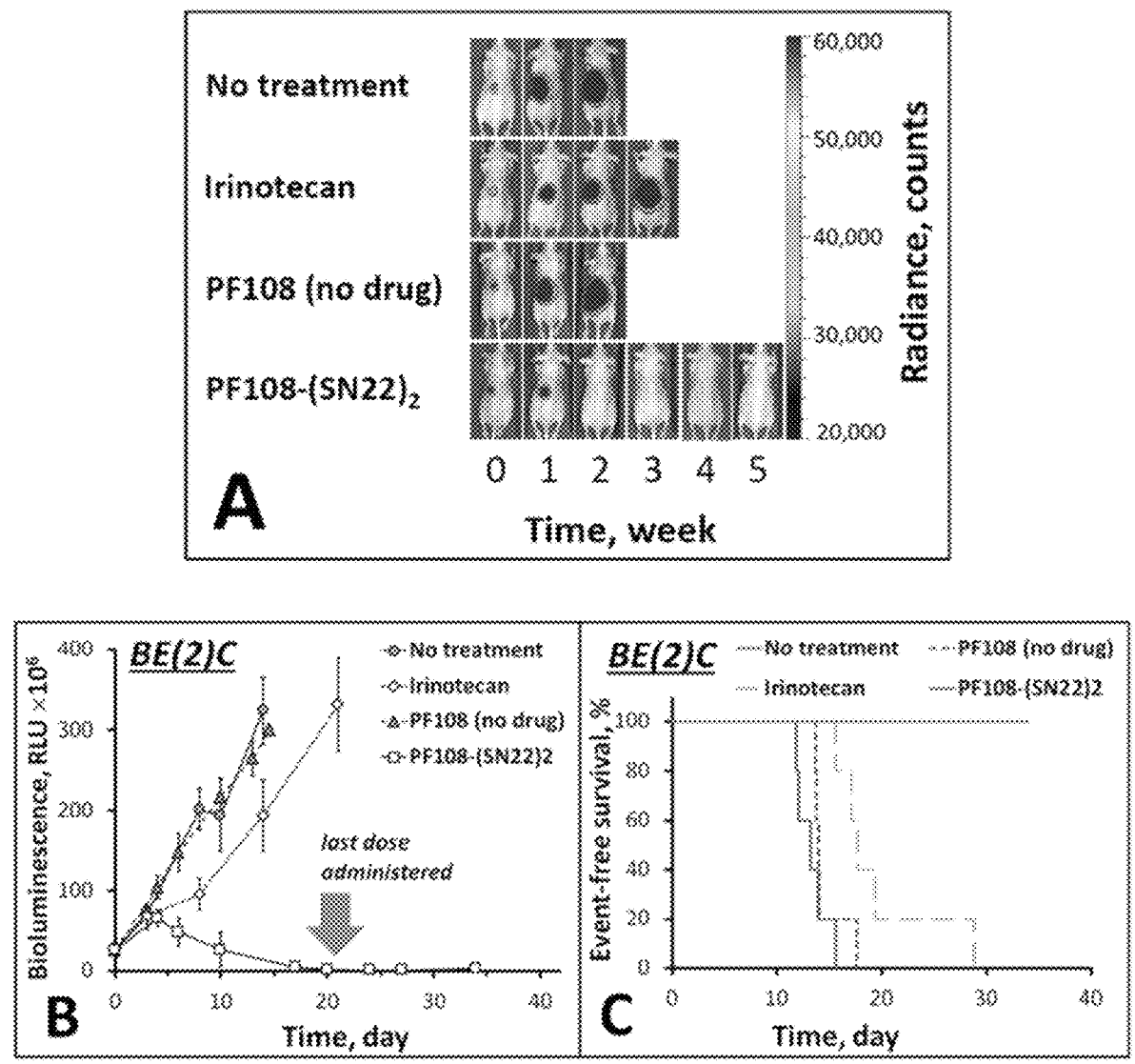
FIG. 3: Therapeutic efficacy of PF108-(SN22)$_2$ in an orthotopic model of refractory, high-risk NB, Mice were inoculated with $10^6$ BE(2)C cells stably expressing luciferase according to a procedure described in [44]. Treatment with PF108-(SN22)$_2$ was administered intravenously at a dose equivalent to 10 mg/kg of SN22 once a week for 4 weeks. Irinotecan administered twice a week at 10 mg/kg of SN38 was included as a positive control. Saline or chemically unmodified Pluronic F-108 were used as negative controls. Tumor-associated signal was monitored quantitative bioluminescence (representative images taken at 0-5 week are shown in (A). Quantitative data presented graphically in (B) are expressed as mean±SD. The survival curves for respective animal groups over a 5-week period in this study are shown in (C).

In agreement with its sustained presence at intratumoral levels above 1.5 µg/g, SN22 formulated and administered once a week as a Poloxamer-based prodrug caused tumor regression and potently suppressed regrowth of orthotopic BE(2)C xenografts (FIGS. 3A and B). This in turn translated into markedly extended animal survival (FIG. 3C), in contrast to a marginal antitumor effect of irinotecan given twice more frequently in this study. The marginal effect of irinotecan in this NB model (FIG. 3) demonstrates adequacy of a preclinical evaluation approach recapitulating the significant challenge in achieving a lasting therapeutic response in the setting of aggressive, refractory human NB. Notably, unlike irinotecan, PF108-(SN22)$^2$ was able to both cause tumor shrinkage and stabilize the disease, with no progression observed during and beyond the treatment period consisting of only four weakly doses (last dose of PF108-(SN22)$_2$ administered on day 21; indicated in FIG. 3B). The remarkable anticancer action of a Poloxamer-SN22 prodrug was not accompanied by signs of systemic toxicity, such as diarrhea, skin testing (due to dehydration), skin ulcerations, anorexia, cachexia, or weight gain retardation.

5. Poloxamer-SN22 Prodrug Quantitative Studies of the Antiproliferative Effects on MYCN-Amplified NB Cells.

To demonstrate feasibility of comparatively studying the antiproliferative effect of polymeric prodrugs on NB cells with distinct (chemo-naïve vs. chemoresistant) phenotypes, the effect of PF108-(SN22)$_2$ on two cell lines representing aggressive, MYCN-amplified disease before treatment initiation and at relapse after intensive chemo-radiotherapy (MR-32 and BE(2)C respectively) were compared.

A strong difference in response patterns was observed between chemo-naïve and chemoresistant cells; although growth of IMR-32 was inhibited uniformly with high potency within the entire studied dose and duration exposure ranges (FIG. 4A), BE(2)C cells exhibited only limited growth inhibition by PF108-(SN22)$_2$ at doses ≥40 ng drug per well or exposure durations ≥4 hr. Notably, the responsiveness of these cells to free SN22 with or without chemically unmodified Pluronic F-108 was also strongly shifted in comparison to IMR-32 toward higher doses and longer exposure durations, in agreement with the chemoresistant phenotype of BE(2)C exhibiting, a loss of p53 function and reduced sensitivity to different families of chemotherapeutics as shown in previous studies.

6. Comparative Tumor Uptake and Retention of SN22 formulated as a Poloxamer Prodrug.

Figure 2:
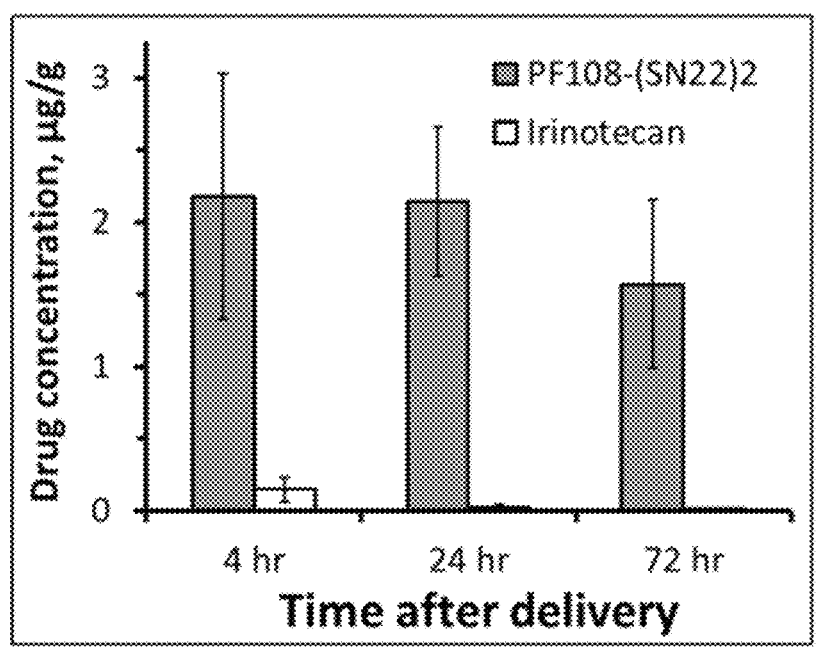
FIG. 2: Intratumoral delivered as a Poloxamer-based prodrug, in comparison to SN38 administered as irinotecan, its clinically used water-soluble precursor (4 hr-3 days). The analysis was carried out in an orthotopic xenograft model of refractory NB. Athymic nude (nu/nu) mice (n=5) were inoculated in the suprarenal fat pad with BE(2)C cells ($10^6$ per animal) suspended in 20% Pluronic F-127 (50 µl). The tumors were allowed to reach the size of 1.0±0.4 cm$^3$ under the control of bioluminescent imaging. PF108-(SN22)$_2$ or irinotecan (120 µl) were administered by tail vein injection at a dose equivalent to 10 mg/kg of SN22 or SN38, respectively, Tumors were harvested, weighed and analyzed by HPLC for intratumoral drug levels at 4, 24 and 72 hr. Weight-normalized drug concentrations are presented in comparison for the two groups as mean±SD.
Figure 5:
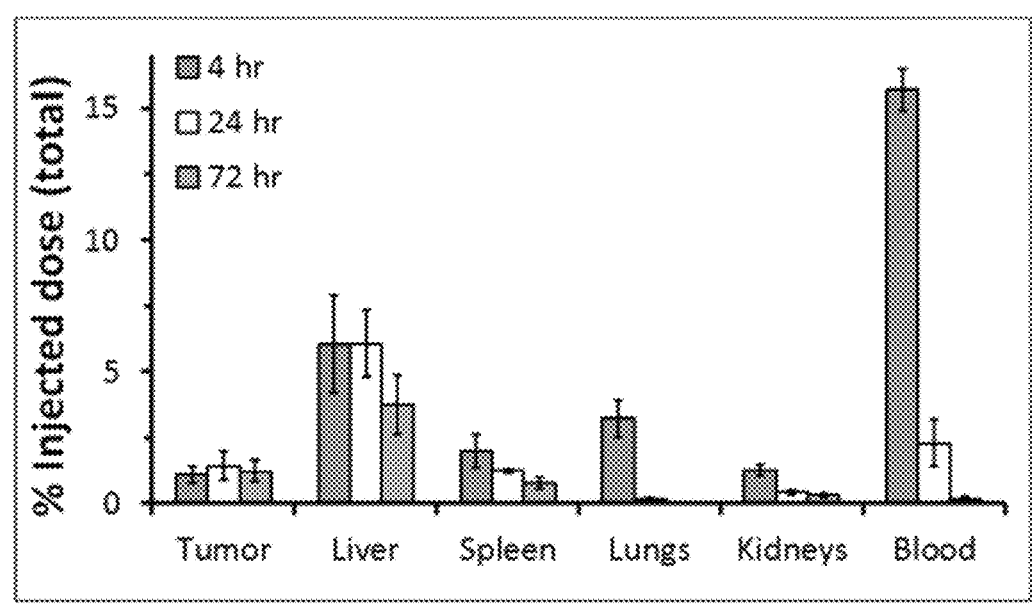
FIG. 5: Organ distribution and intratumoral levels of SN22 delivered as PF108-(SN22)$_2$ (4 hr-3 days). The analysis was carried out in orthotopic BE(2)C xenografts allowed to reach the size of 1.0±0.4 cm$^3$ under the control of bioluminescent imaging. The prodrug was administered by tail vein injection at a dose equivalent to 10 mg/kg of SN22. The analysis was carried out by fluorimetry. Drug amounts are shown as % injected dose per organ, presented as mean±SD.

The effectiveness of the delivery approach using Poloxamer-based prodrugs is demonstrated by data showing rapid tumor uptake and lasting intratumoral retention of SN22 administered as a PF108-(SN22)$_2$ conjugate (FIGS. 2 and 5). PF108-(SN22)$_2$ achieves extended drug presence in orthotopic NB tumors at levels about two orders of magnitude greater than the reported effective local concentration required for suppressing growth of chemoresistant NB cells.

Organ distribution analysis confirmed rapid accumulation and protracted retention of SN22 delivered as a prodrug, with relatively low drug amounts taken up by the organs of the reticuloendothelial system, liver and spleen. A significant amount of SN22 administered as PF108-(SN22)$_2$ was measured in blood at 4 and 24 hr post-administration, consistent with ongoing drug accumulation in the tumor over this time period (FIG. 5). This is in contrast to rapid drug elimination observed in peripheral organs, spleen, lungs and kidneys. Importantly, topoisomerase I inhibitors are highly specific to cycling cells (S phase-dependent), unlike other chemotherapeutics that can be highly cytotoxic even in the absence of active replication.

Together with the limited distribution and rapid drug clearance from peripheral organs observed with Poloxamer prodrug-based delivery, the pharmacologically selective mode of action potentially further reduces the risk of significant systemic toxicity, consistent with a lack of acute systemic toxicity symptoms (diarrhea, ulcerations, anorexia, cachexia, or weight loss).

7. Poloxamer-SN22 Prodrug Causes Shrinkage and Suppresses Regrowth of Small and Large NB Tumors Showing a Transient Response to Irinotecan.

Figure 6:
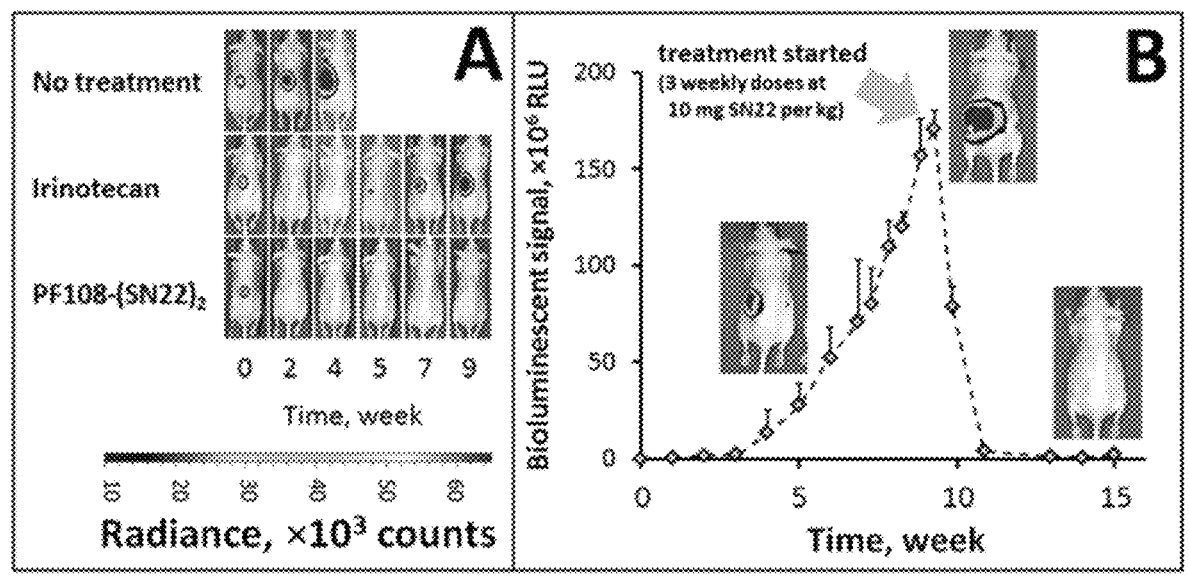
FIG. 6: Therapeutic efficacy of PF108-(SN22)$_2$ in an orthotopic model of chemo-naïve, MYCN-amplified NB. Mice were inoculated with $10^6$ luciferase-expressing IMR-32 cells. Treatment with irinotecan or PF108-(SN22)$_2$ (10 mg drug per kg, 2× and 1× week, respectively, over 4 weeks) was initiated 3 weeks after inoculation (A). Alternatively, PF108-(SN22)$_2$ was administered once a week over 3 weeks to animals with 10-fold larger NB tumors (B). Tumor-associated signal was monitored by quantitative bioluminescence. Quantitative data are shown as mean±SD.

The effectiveness of the poloxamer-based prodrug strategy in providing sustained anticancer effects on small and large NB tumors was shown experimentally with a once a week dosing regimen of PF108-(SN22)$_2$ (orthotopic IMR-32 xenograft model, FIG. 6). Notably, despite their chemo-naïve phenotype, orthotopic NB tumors established with MYCN-amplified IMR-32 cells showed only a transient response to irinotecan (given ×2 times a week). Together with the results demonstrating effectiveness of the prodrug approach in the BE(2)C xenograft model of refractory disease (FIG. 3), this provides strong evidence in support of Poloxamer prodrug-based delivery in the context of high-risk NB showing limited or no response to conventional chemotherapy.

Example 2: PEG-[SN22]$_4$

1. Synthesis of PEG-[SN22]$_4$.

Conjugation of carboxylated 4-arm-PEG (JenKem Technology, Mn=20,553 Da) with SN22 using 1,3-dicyclohexylcarbodiimide (DCC) as an activating agent for the carboxylic groups, 4-dimethylaminopyridine tosylate (DPTS) as a catalyst and CH$_2$Cl$_2$ as a solvent formed a polymeric conjugate containing 0.17 mmol/g or 6.4% wt. of the drug. 1H NMR Showed that SN-22 was covalently bound to the polymer by ester bonds between carboxylic groups of the carboxylated polymer and 20-OH of SN22.

2. Experimental Results.

Figure 7:
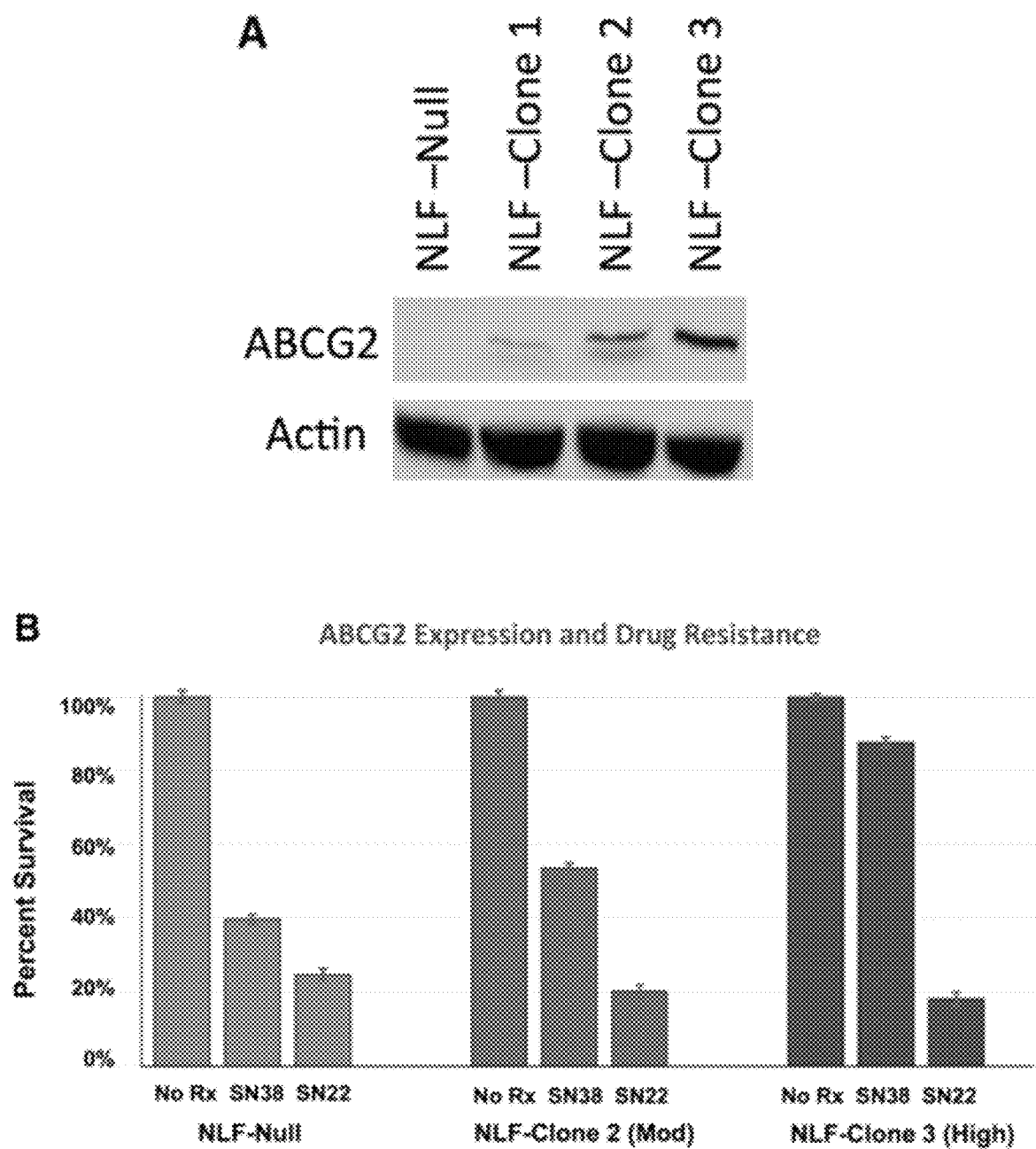
FIG. 7: ABCG2 expression and growth of NLF and transfected clones. (A) Western analysis was performed on NLF and three single-cell clones with an ABCG2 antibody (Santa Cruz), compared to an actin control. Clones 1, 2 and 3 had trace, low and, intermediate levels of ABCG2 expression, respectively. (B) Growth of NLF and ABCG2-expressing clones in the presence of SN38 or SN22 (50 ng/ml). Growth shown at day 4.

To evaluate susceptibility of SN38 and SN22 to ABCG2 efflux, an ABCG2-null NB cell line, NLF, was identified. NLF was transfected with an ABCG2 expression vector, and then selected single-cell clones with trace, low, and intermediate levels of ABCG2 expression (FIG. 7A). Next, the sensitivity of NLF and ABCG2-expressing clones to different concentrations of SN38 or SN22 and monitored growth continuously using IncuCyte® S3 Live-Cell Analysis System was assessed. Clones with higher levels of ABCG2 were increasingly resistant to SN38, whereas they remained fully sensitive to SN22 (FIG. 7B) This suggests that endogenous ABCG2 expression, which characterizes aggressive NBs and NB stem cells, contributes to drug resistance to irinotecan/SN38 and possibly other chemotherapeutics vulnerable to ABCG2 efflux.

To explore different schedules of SN22 in NBs in vivo, testing using a NB flank xenograft mouse model, a subclone of the chemo-naïve SH-SY5Y NB line in immunodeficient nu/nu mice was performed. Two different treatment schedules of PEG-[SN22]4 (10 mg/kg/dose) compared to CPT-11 (25 mg/kg/dose) IV twice a week for 4 weeks in a preliminary experiment were evaluated. The PEG-[SN22]4 was administered either twice a week for two weeks, or once a week for four weeks (4 doses each). Even though twice as many CPT-11 doses were administered at a 2.5× higher dose, PEG-[SN22]4 was much more effective at inducing remissions and prolonging survival.

Figure 8:
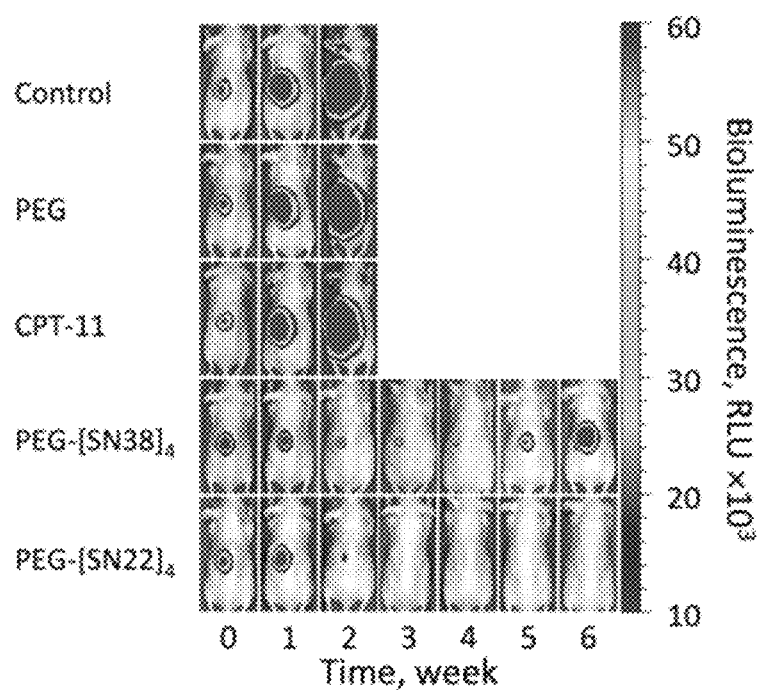
FIG. 8: Treatment of orthotopic NB model. Chemoresistant, luciferase transfected, SKNBE(2)C cells (107) were injected in the perirenal fat pad of nude mice. Mice were divided into five groups: no treatment, or treatment with blank PEG, CPT-11, PEG-[SN38]4 or PEG-[SN22]4 (10 animals per group). Treatment started when tumors reached about 0.2 cm$^3$. Treatment with either PEG-[SN38]4 or PEG-[SN22]4 produced tumor regression, but only PEG-[SN22]4 treatment caused complete tumor disappearance.

Next, PEG-[SN22]4, PEG-[SN38]4 and CPT-11 in a NB orthotopic xenograft mouse model with the chemo-resistant NB line SKNBE(2)C. BE(2)C cells were transfected with a luciferase expression vector to allow for bioluminescent imaging. Mice were treated once a week for 4 weeks with either PEG-[SN22]4 (10 mg/kg/dose), PEG-[SN38]4 (10 mg/kg/dose) or CPT-11 (15 mg/kg/dose). In this chemoresistant model, CPT-11 had no effect, whereas both PEG-[SN22]4 and PEG-[SN38]4 were extremely effective at shrinking the tumor (FIG. 8). While tumors rapidly regrew after treatment cessation in the PEG-[SN38]4 treated mice, PEG-[SN22]4 treatment resulted in complete disappearance of tumors and a lasting inhibition of their growth beyond the duration of the treatment period, suggesting that PEG-[SN22]4 has superior efficacy against refractory disease, presumably due to its ability to overcome acquired drug resistance.

Figure 9:
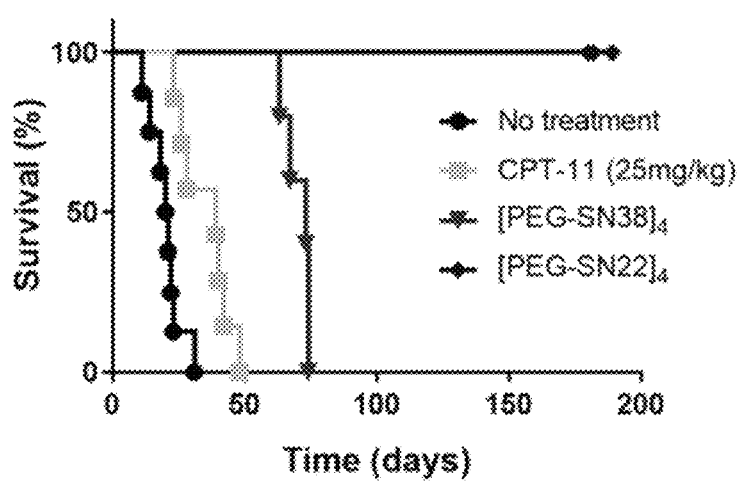
FIG. 9: Efficacy of PEG-[SN22]4 and PEG-[SN38]4 in TH-MYCN transgenic mouse model. Mice were treated with saline (N=8), CPT-11 (15 mg/kg/dose; N=7), PEG-[SN38]4 (10 mg/kg/dose; N=6) or PEG-[SN22]4 (10 mg/kg/dose; N=6) IV by tail vein once a week×4 weeks. Treatments started when the mice were about 5 weeks old with a tumor size about 1-2 cm$^3$. Mice were removed from the study when they showed signs of distress due to tumor burden. PEG-[SN22]4 had rapid tumor regression, and no tumor was found at autopsy at 180-200 days.

PEG-[SN22]4 was also used to treat de novo NBs in a TH-MYCN transgenic mouse model. Spontaneous tumors develop in paraspinal ganglia or in the adrenal gland by 4-5 weeks in almost all mice with two, copies of the transgene. Mice were divided into 4 groups once tumors became palpable (4-5 weeks): control-no treatment; CPT-11 treatment (15 mg/kg/dose), PEG-[SN38]4 (10 mg/kg/dose), or PEG-[SN22]4 (10 mg/kg/dose). Mice were treated once a week for 4 weeks. Tumors progressed rapidly in the untreated animals, and tumor growth was only slightly delayed by CPT-11 treatment. Mice were sacrificed when they became symptomatic from tumor burden. However, all tumors regressed with PEG-[SN22]4 treatment and became nonpalpable within 1-2 weeks of treatment (FIG. 9). They remained non-palpable in all mice for over 180 days after the initiation of SN22 treatment. Several of these mice were sacrificed, and the site of tumor was examined grossly and microscopically, but no evidence of tumor was found in any mice. These data suggest that PEG-[SN22]4 is extremely effective against spontaneous tumors arising in immunocompetent mice, and even 4 weekly doses were sufficient to produce long-term remissions and cures in all the animals.

Figure 10:
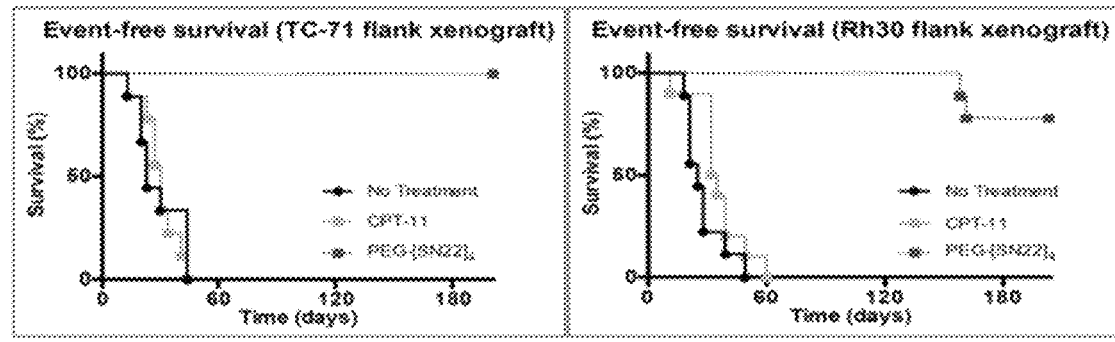
FIG. 10: Survival EWS and RMS xenografts treated with PEG[SN22]4. Mice were treated with saline, CPT-11 (15 mg/kg/dose), or PEG-[SN22]4 (10 mg/kg/dose) (N=10 for all) IV by tail vein once a week×4 weeks. Left. Survival of animals with flank xenografts of the EWS cell line TC-71 (chemo-resistant) after 4 weeks of treatment. None of the PEG-[SN22]4 animals recurred. Right. Survival of animals with flank xenografts of the alveolar (fusion-position) RMS cell line Rh30 after 4 weeks of treatment. Two of the animals treated with PEG-[SN22]4 had a late recurrence, and one had a small, slow-growing tumor, but the 7 others were tumor free at 180-200 days.

PEG-[SN22]4 was used to treat two representative sarcomas growing as xenografts in a similar manner. A chemoresistant Ewing sarcoma (EWS) line TC-71 and an alveolar (fusion positive) rhabdomyosarcoma (RMS) line Rh30 were treated. After 180 days, all EWS mice were without palpable tumors, but two mice with RMS xenografts had tumor regrowth around 150 days and had to be sacrificed (FIG. 10). Since these mice were treated with only 4 weekly doses of a single drug, it is possible that these recurrences could have been avoided by longer treatment or combination with another agent. Nevertheless, these results in EWS and RMS demonstrate that the efficacy of PEG-[SN22]4 is not restricted to or unique for NBs, but applies to other solid tumors.

The results presented above show considerable efficacy of PEG-[SN22]4 in eradicating tumors from NB xenografts as well as spontaneous NBs arising in immunocompetent transgenic animals. Most animals were "cured" as defined by event-free survival (EFS) for 180-200 days from the start of treatment. Similar results were obtained in treating a single chemo-resistant EWS line and a single fusion-positive RMS line as flank xenografts. Thus, PEG-[SN22]4 is effective as a single agent in obtaining long-term EFS in these animal models of aggressive childhood solid tumors, and other conditions as described herein.

Cell lines. A panel of 4 NB cell lines representing major genotypes (MYCN amplification, 1p36 deletion, ALK mutation) of high-risk NB, as well as both chemo-naïve and chemo-resistant tumors (SY5Y, IMR5, NLF, SKNBE2C) can be used for all in nitro and in vivo studies. Cells are grown in RPMI-1640 (Gibco) with 10% fetal calf serum (Cellgro), and maintained in a humidified atmosphere of 95% air and 5% $CO_2$. Cells are harvested with 0.02% $Na_4$ EDTA in phosphate buffered saline (PBS). The RMS lines to be used are RH18 and RH30 (embryonic, alveolar); the EWS lines are TC32 and TC71 (diagnosis, relapse); and the OS lines are U2OS and SAOS2.

Mice. Six-week-old Foxn1$^{nu}$/Foxn1$^{nu}$ (JAX stock #007850) mice from Jackson Laboratories are used. Mice are maintained under humidity- and temperature-controlled conditions in a light/dark cycle that is set at 12-hour intervals. These mice are in a 129-SvJ background. Mice homozygous for the transgene generally develop tumors within 4-5 weeks.

Flank xenografts. Mice are injected SQ in the right flank with $1\times10^7$ of NB cells suspended in 0.1 ml of Matrigel (Corning, Tewksbury, Mass.). Tumors are measured manually 2×/week in 2 dimension (mm) using a caliper. The volume (cm$^3$) is calculated as follows: $[(0.523 \times L \times W^2)]$ where L>W. Body weights are obtained 2×/week, and treatment doses adjusted if there is a >10% change in, body weight, Mice (n=10 per arm) are treated with PEG-[SN22]4 by tail vein injections 1×/week for 4 weeks, once tumor volumes reach 0.2 cm$^3$ (2). PEG-[SN22]4 is given at 10 mg/kg/dose; CPT-11 (CPT-11; 5 mg/kg) or vehicle only are used as positive and negative controls.

Orthotopic xenografts. NB cells stably expressing luciferase are implanted at 10$^6$ cells per animal into the suprarenal fat pad of athymic nude (nu/nu) mice. Tumor is verified and tumor burden monitored twice a week thereafter by bioluminescent imaging using a Xenogen IVIS Imaging System (Perkin Elmer, Santa Clara, Calif.) coupled with the Living Image Software (Caliper Life Sciences, Hopkinton, Mass., USA). After reaching a tumor size of 1 cm$^3$ (~28 days post inoculation), tumor-bearing mice are randomized into groups of 10 animals and administered IV with a single 120-μl dose of PEG-(SN22)4, CPT-11 or vehicle, as above.

Pharmacokinetics analysis or PEG-[SN22]4 and CPT-11. Mice (n=3 per arm, per time point) with flank xenografts are given a single dose of PEG-[SN22]4 at 10 mg/kg, or CPT-11 as 15 mg/kg IV via tail vein. The dose is lower because CPT-11 is a prodrug that requires inversion to active SN38 by the liver. Blood is obtained by retroorbital a terminal bleeds, and collected into 2 ml collection tubes containing sodium heparin (BD). Tissues (tumor, lung, liver, spleen, kidney) are collected post-sacrifice at 4, 12, 24, 48, and 72 hours after heart perfusion with cold saline and analyzed by the CHOP Pharmacology Core. Total SN38, SN22 and CPT-11 levels are analyzed in mouse blood (1:1 diluted with water) and tissue homogenates by UPLC-MS/MS.

Example 3: [PEG-SN38-BG]$_8$

1. Tripartite Polymer-Based Prodrug Synthesis.

Prodrugs as described herein carry either eight or two drug-ligand hybrid molecules linked to a multiarm or linear PEG carrier, respectively, via an in situ cleavable ester bond. Their hydrolytic lability and activation rates are increased in comparison to those of regular (acyl) esters due to a strong electron displacement effect of the alkoxyacetyl group.

First, N-Boc-protected aminomethylphenoxyhexanoic acid was conjugated to SN-38 (AstaTech, Bristol, Pa.) with an 85% yield using 4-N,N-dimethylaminopyridine tosylate (DPTS) as a catalyst, 1,3-dicyclohexylcarbodiimiide (DCC) as an activating agent for the carboxylic groups, and dichloromethane as a solvent. The protecting group was removed with trifluoroacetic acid, and the conjugate was reacted in a 1:1 mixture of tetrahydrofuran and dichloromethane with 1,3-di-Boc-2-(trifluoromethylsolfonyl)guanidine as a guanidinylation agent (yield: 75%). The small-molecule conjugate of Boc-protected BG and SN-38 connected via a hydrolytically cleavable 6-hexanoyl spacer was than attached to a carboxylated 8-arm PEG (JenKem Technology, $M_n$=37390 Da, PDI=1.06), also using DPTS, DCC and dichloromethane as the catalyst, activator and solvent, respectively.

For purification, the polymer was precipitated with diethyl ether from solution in benzene, and residual DPTS was removed by washing with aqueous sodium sulfate (21% w/w). The absence of mobile compounds was confirmed at this step by TLC analysis (silica gel chloroform-acetonitrile, 7:3). Finally, the protecting groups were removed from the guanidine moieties by treatment with trifluoroacetic acid. The obtained [PEG-SN38-BG]$_8$ polymer was washed with diethyl ether and dried in vacuo. The structure and functionalization efficiency of the product were analyzed by $^1$H NMR, showing 0.18 mmol/g (7.1% by weight) of SN-38 and an equivalent amount of BG associated with the polymer. The purity was confirmed by both TLC and $^1$H NMR analysis.

2. Uptake for Targeted Tumor Therapy.

SN-38 delivered as an 8-arm PEG-based and BG-functionalized prodrug, [PEG-SN38-BG]$_8$, at an equivalent dose corresponding to 10 mg SN-38 per kg was stably present in the tumors at many fold higher concentrations: 2.82±0.53 μg, 4.46±1.59 μg/g, and 2.63±0.85 μg/g at 1 hr, 4 hr and 24 hr, respectively (FIG. 11), suggesting that polymeric prodrug-based delivery can provide stable therapeutically effective drug levels required for suppressing growth of refractory tumors not responding to standard treatments.

Figure 12:
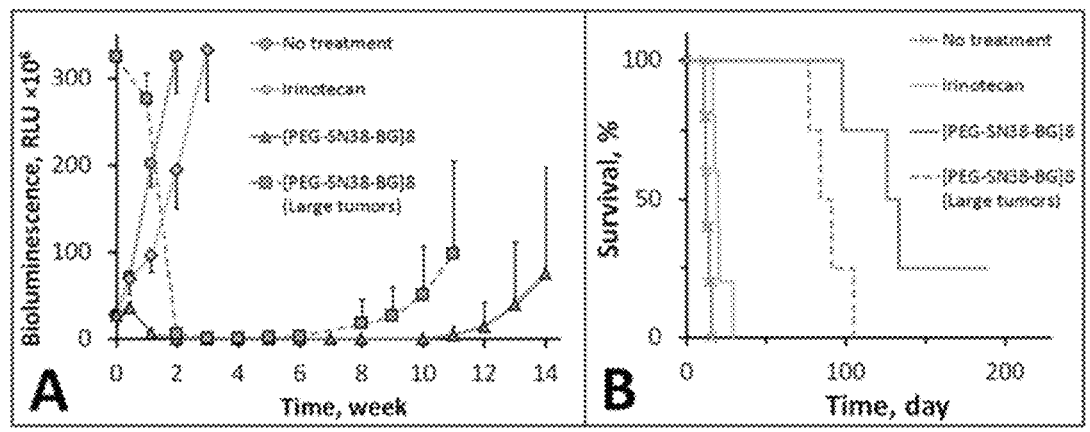
FIG. 12: Therapeutic efficacy of [PEG-SN38-BG]$_8$ in an orthotopic model of refractory, high-risk NB. Athymic nude (nu/nu) mice were inoculated with BE(2)C cells ($10^6$) stably expressing luciferase. Treatment with [PEG-SN38-BG]$_8$ was administered intravenously at a dose equivalent to 10 mg/kg of SN-38 twice a week for 4 weeks. Irinotecan administered twice a week at 15 mg/kg was included as a positive control. A group or mice administered with saline (no treatment) was used as a negative control. In an additional group, the prodrug was administered using the same regimen to animals allowed to reach a 10-fold larger tumor size (2.0 cm$^3$, 'large tumors'). Tumor-associated signal was monitored by quantitative bioluminescence. Data presented graphically in (A) are expressed as mean±SD. The survival curves for respective animal groups over a 190-day period are shown in (B).

In agreement with sustained intratumoral presence of SN-38 at levels two orders of magnitude greater than the reported therapeutic threshold of 25 ng/ml for the drug-resistant NB cell line BE(2)C, the drug formulated and administered as [PEG-SN38-BG]$_8$ caused rapid tumor regression and potently suppressed regrowth of small and large orthotopic BE(2)C xenografts (FIG. 12A). The durable anticancer effect of the prodrug markedly extended the event-free animal survival ($t_{50\% \ survival}$ of 130 and 88 days, respectively, vs. 12 days for untreated animals, FIG. 12B), in contrast to a marginal therapeutic effect and survival extension by irinotecan administered at an equivalent dose in this study ($t_{50\% \ survival}$ of 20 days).

Importantly, the marginal effect of irinotecan in this model demonstrates adequacy of a preclinical evaluation approach recapitulating the therapeutic challenge in achieving a lasting, clinically meaningful response in the setting of aggressive, refractory human NB. At the same time, [PEG-SN38-BG]$_8$ was able to cause rapid tumor shrinkage and stabilize the disease, with no progression observed during and beyond the treatment period consisting of eight doses (last dose administered on day 24). Remarkably, no signs of systemic toxicity, such as diarrhea, skin tenting (due to dehydration), skin ulcerations, anorexia, cachexia, or weight gain retardation, were observed during the treatment with [PEG-SN38-BG]$_8$ prodrug.

3. NET Expression Enhancing Agents can Further Improve the Performance of Uptake-1 Targeted Prodrugs.

Vorinostat, a potent pan-HDAC inhibitor with a toxicity profile that is largely non-overlapping with that of topoisomerase I inhibitors, was shown to both substantially increase NET expression in NB tumors and sensitize tumor cells to camptothecin drugs by inhibiting the expression of DNA break repair enzymes and promoting DNA damage-induced apoptosis [44], both effects relevant to enhancing targeted therapy of neuroendocrine tumors with BG-functionalized prodrugs of SN-38. The potentiating effect of vorinostat on BE(2)C cell growth inhibition by [PEG-SN38-BG]$_8$ vs. SN-38 was examined.

Figure 13:
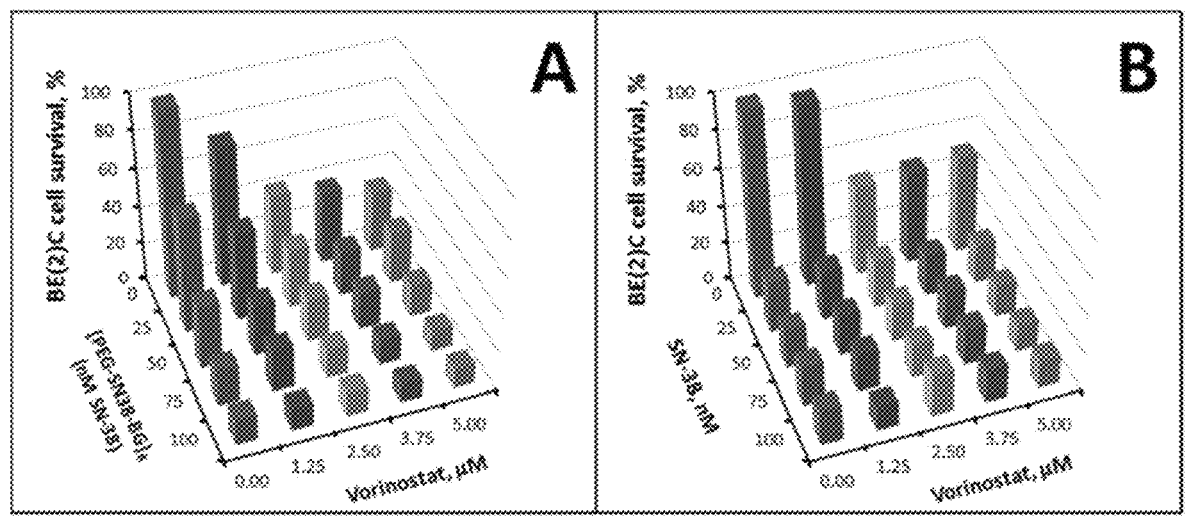
FIG. 13: Evaluation of the potentiating effect of vorinostat on the antiproliferative activities of [PEG-SN38-BG]$_8$ and SN-38 ((A) and (B), respectively) in chemoresistant NB cells, BE(2)C. In accordance with vorinostat-induced NET expression reported to peak at 6 hr, an exposure period of 6 hr was chosen for the present experiment. BE(2)C cells were incubated with [PEG-SN38-BG]$_8$ or SN-38 at concentrations equivalent to 25-100 nM of SN-38, with/without vorinostat (1.25-5.0 μM). Cell growth was measured by bioluminescence. BE(2)C cell survival data at 6 days post treatment were analyzed for hyperadditivity by applying a model $z=z_0+A \cdot x+B \cdot y+C \cdot [x \cdot y]$ and determining the significance of the interaction term C.

Vorinostat markedly potentiated the antiproliferative effect of [PEG-SN38-BG]$_8$ ($p<0.0001$ for the interaction term C in $z=z_0+A \cdot x+B \cdot y+C \cdot [x \cdot y]$, FIG. 13A), but also moderately synergized with the chemically unmodified SN-38 ($P=0.087$ for C, FIG. 13B). This is consistent with the combined, NET expression-related and unrelated, mechanisms of drug potentiation exhibited by vorinostat, adding toward the greater enhancement of NB cell growth inhibition by the BG-functionalized prodrug. Notably, in the low micromolar concentration range (1-5 µM) where vorinostat strongly enhanced the action of the prodrug, its own BE(2)C cell growth inhibitory effect was only moderate (FIG. 13A), in agreement with the modest single-agent activity of vorinostat in preclinical models of NB.

4. Prodrug-Mediated Growth Inhibition of Chemoresistant NB Cells and its Pharmacological Potentiation.

To evaluate the specific contribution of the targeting ligand incorporated in the prodrug structure, the cell growth inhibitory activity of [PEG-SN38-BG]$_8$ on NET-expressing, chemoresistant NB cells was compared to that of a control molecule, [PEG-SN38]$_8$, constructed analogously but without the BG moiety. Additionally, having established that a pan-HDAC inhibitor shown to upregulate NET expression and enhance uptake-1 in NB cells and tumor xenografts strongly potentiates the antiproliferative effect of [PEG-SN38-BG]$_8$ on NET-expressing NB cells (FIG. 13), the hypothesis that a selective HDAC inhibitor with specificity for the HD type 1 subfamily (entinostat) will also synergize with [PEG-SN38-BG]$_8$ was addressed.

Figure 14:
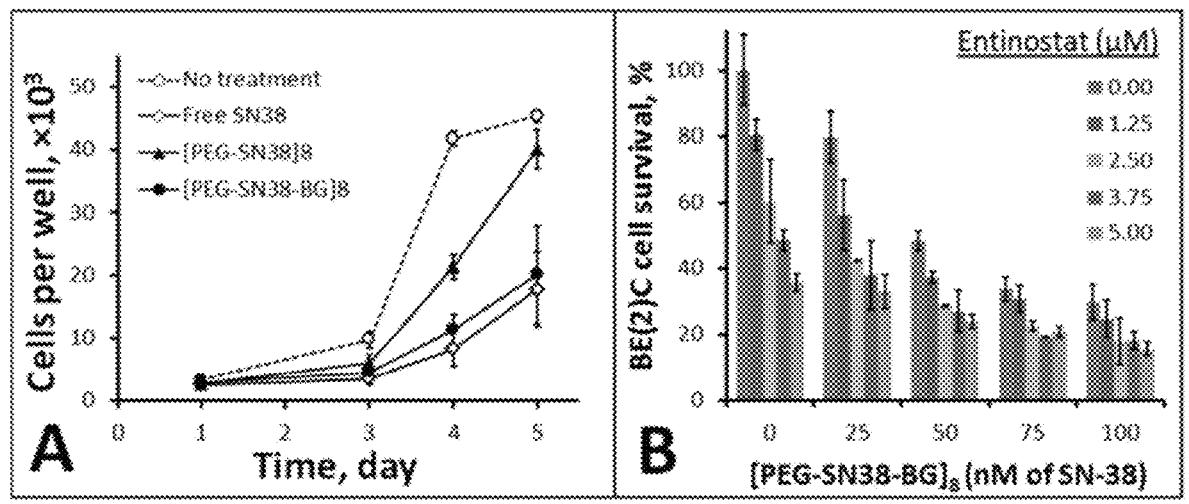
FIG. 14: Antiproliferative effect of [PEG-SN38-BG]$_8$ prodrug on NET-expressing, chemoresistant NB cells, BE(2)C. The effect on cell growth kinetics was studied in comparison to free SN-38 or bipartite [PEG-SN38]$_8$ lacking functionalization with BG (A). Cells were exposed for 4 hr to equivalent concentrations of the compounds, corresponding to 125 nM of SN-38. In en additional experiment (B), the response, to treatment with [PEG-SN38-BG]$_8$ was examined with/without a HDAC1-specific inhibitor, entinostat (0-5 μM), The doses of the prodrug were varied within a range equivalent to 0-100 nM SN-38, and the exposure duration was fixed at 6 hr. Cell growth was monitored by bioluminescence. The response is shown as % cell survival (mean±SD) at 6 days post-treatment. Experimental data were analyzed for hyperadditivity using a model $z=z_0+A \cdot x+B \cdot y+C \cdot [x \cdot y]$ and determining the significance of the interaction term C.

A strong difference in the ability to suppress proliferation of chemoresistant NB cells was observed between the tripartite prodrug and a bipartite control construct assembled without the BG ligand. Whereas growth of the NET-expressing BE(2)C calls was inhibited by [PEG-SN38-BG]$_8$ with high potency comparable to that of free SN-38 under the in vitro conditions of direct drug-cell contact, the bipartite construct, [PEG-SN38]$_8$ was notably less effective (FIG. 14A), pointing to the importance of the tripartite design and the role of BG in enhancing the antiproliferative response. In a separate study, a strong potentiating effect on the prodrug-mediated NB cell growth suppression was shown for an HDAC1-specific blocker, entinostat (FIG. 14B, $p<0.001$ for the interaction term C). Interestingly, this finding suggests that entinostat, a highly selective non-chemotherapeutic agent with an epigenetic mode of action, can synergize with BG-functionalized therapeutics possibly through enhancing their uptake, similar to the chemically distinct pan-HDAC inhibitor, vorinostat.

5. Comparative Tumor Uptake and Retention of SN-38 Formulated as a NET-Targeted Prodrug.

Figure 11:
FIG. 11: Intratumoral levels or SN-38 delivered as a NET-targeted macromolecular prodrug designed using 8-arm (40 kDa) PEG as a carrier and BG as a targeting ligand ([PEG-SN38-BG]$_8$). The analysis was carried out in an orthotopic xenograft model of refractory NB. Athymic nude (nu/nu) mice (n=5) were inoculated in the suprarenal fat pad with BE(2)C cells ($10^6$ per animal) suspended in 20% Pluronic F-127 (50 µl). The tumors were allowed to reach the size of 1.0±0.4 cm$^3$ under the control of bioluminescent imaging. [PEG-SN38-BG]$_8$ was administered by tail vein injection at a dose equivalent to 10 mg/kg of SN-38. Tumors were harvested, weighed and analyzed by HPLC. Weight-normalized drug concentrations are presented as mean±SD.

The effectiveness of the prodrug-based therapeutic strategy was demonstrated in studies showing rapid tumor uptake and lasting intratumoral retention of SN-38 delivered as a [PEG-SN38-BG]$_8$ tripartite prodrug (FIG. 11 and Table 2). In contrast to SN-38 administered in the form of its clinically used, pharmacologically inactive precursor (innotecan), prodrug-based delivery achieves localization and sustained intratumoral presence of SN-38 at levels about two orders of magnitude higher than the reported SN-38 concentration required for suppressing growth of chemoresistant NB cells, BE(2)C. The analysis was carried out in large orthotopic BE(2)C xenografts (1.0±0.4 cm$^3$, n=5) using an HPLC assay.

TABLE 2

| Time post administration | Intratumoral drug levels expressed as % dose per gram tumor (presented as mean ± SD) | | |
|---|---|---|---|
| | Irinotecan (15 mg/kg) | | [PEG-SN38-BG]$_8$ (10 mg SN-38 per kg) |
| | SN-38 | Irinotecan | Total SN-38 |
| 4 hr | 0.075 ± 0.019 | 0.142 ± 0.031 | 1.78 ± 0.28 |
| 24 hr | 0.012 ± 0.005 | 0.004 ± 0.001 | 1.05 ± 0.15 |

6. [PEG-SN38-BG]$_8$ Prodrug Causes Tumor Regression and Achieves "cures" in a Model of Aggressive NB Showing only a Transient Response to Conventional Therapy.

Figure 15:
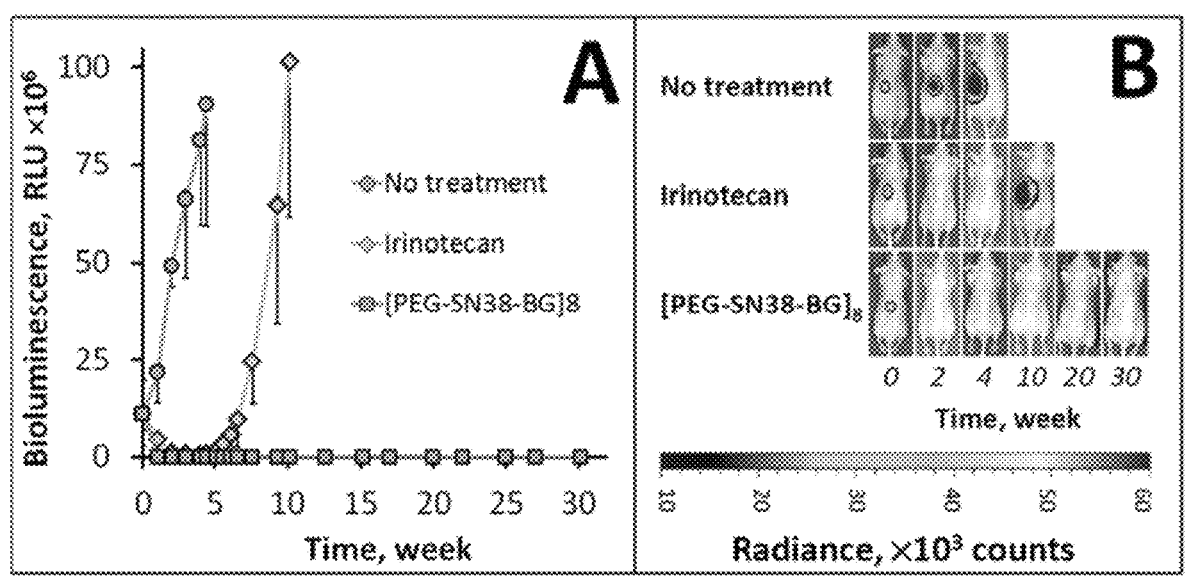
FIG. 15: Therapeutic efficacy of [PEG-SN38-BG]$_8$ in an orthotopic xenograft model of chemo-naïve, MYCN-amplified NB. Mice were inoculated with $10^6$ luciferase-expressing IMR-32 cells. Treatment with the water-soluble precursor of SN-38 (irinotecan) or with [PEG-SN38-BG]$_8$ at doses equivalent to 10 mg SN-38 per kg, 2× week over 4 weeks, was initiated on day 21 after inoculation. Tumor-associated signal was monitored by quantitative bioluminescence. Data in (A) are shown as mean±SD. Representative bioluminescent images each group are included in (B).

The effectiveness of the tripartite prodrug strategy in providing sustained anticancer effects against aggressive NB tumors was shown experimentally in an orthotopic IMR-32 xenograft model (FIG. 15). [PEG-SN38-BG]$_8$ administered twice a week over 4 weeks caused rapid tumor shrinkage with no subsequent regrowth in a model of chemo-naïve MYCN-amplified disease. This is in contrast to tumors starting to regrow immediately after treatment cessation in the animal group treated with the SN-38 precursor, irinotecan (FIG. 15A, B). Together with the results demonstrating effectiveness of the prodrug approach in the BE(2)C xenograft model of refractory disease (FIG. 12), this provides strong evidence in support of tripartite prodrug-based delivery in the context of high-risk NB showing limited or no response to conventional chemotherapy.

7. Tripartite Constructs Show Potential as a Treatment for Multidrug-Resistant, High-Risk Neuroblastoma.

Figure 16:
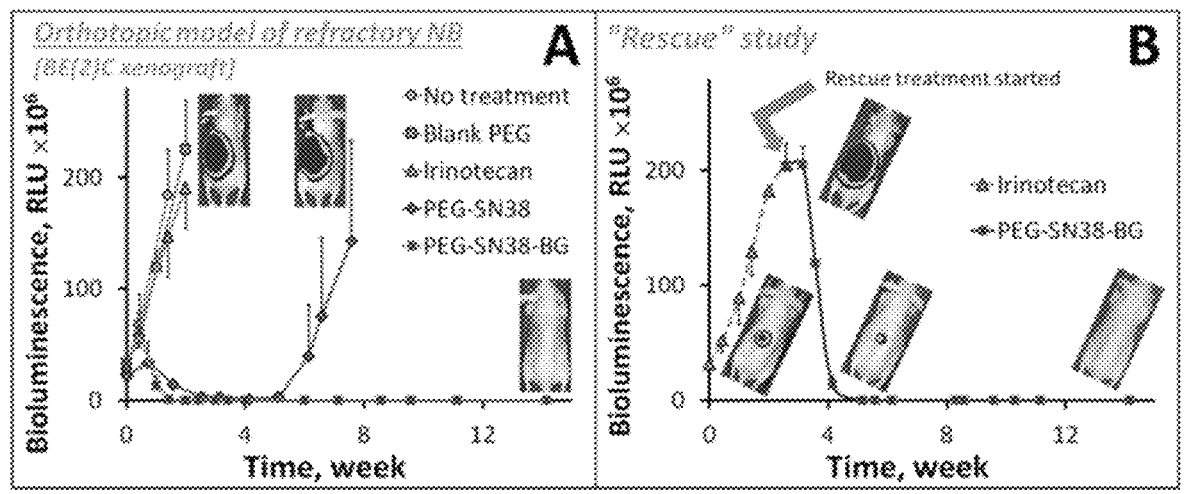
FIG. 16: Therapeutic efficacy of [PEG-SN38-BG]$_8$ in an orthotopic model of refractory, high-risk NB, Athymic nude (nu/nu) mice were inoculated with BE(2)C cells ($10^6$) stably expressing luciferase. Treatment with [PEG-SN38-BG]$_8$ was administered intravenously at a dose equivalent to 10 mg/kg of SN-38 twice a week for 4 weeks. Irinotecan (15 mg/kg) and the equivalent dose of bipartite [PEG-SN38]$_4$ administered twice a week were included for comparison. Groups of mice administered either with blank PEG or saline (no treatment) were used as negative controls (A). In a "rescue" experiment, the prodrug was administered using the same regimen to animals initially treated with irinotecan (1.5 mg/kg, 2×/week), whose tumors had reached 2.0 cm³ at 2 weeks (B). Tumor-associated signal was monitored by quantitative bioluminescence. Data are presented as mean±SD.

SN-38 formulated and administered over 4 weeks (2×/week) as the Norepinephrine Transporter (NET)-targeted polymer-linked prodrug caused rapid tumor regression, fully suppressed regrowth of chemoresistant orthotopic BE(2)C xenografts and markedly extended event-free survival (>14 weeks, FIG. 16A). This is in contrast to irinotecan having no antitumor effect in this model, and is also a dramatic improvement over a bipartite control [PEG-SN38]$_4$, which inhibited tumor growth only for the duration of the treatment period (FIG. 16A). Furthermore, switching animals, who had rapidly developed large tumors (2 cm$^3$) while being treated with irinotecan, to [PEG-SN38-BG]$_8$ caused their tumors to shrink and remain undetectable for >12 weeks ("rescue" study, FIG. 16B).

Importantly, the lack of an antitumor effect exhibited by irinotecan, similar to a lack of response seen in ultrahigh-risk NB patients, shows that preclinical models faithfully recapitulates the clinical behavior of refractory NB. Remarkably, the lasting and profound therapeutic effect seen with [PEG-SN38-BG]$_8$ was not accompanied by signs of systematic toxicity (diarrhea, skin tenting or ulcerations, anorexia, cachexia, or weight gain retardation).

Figure 17:
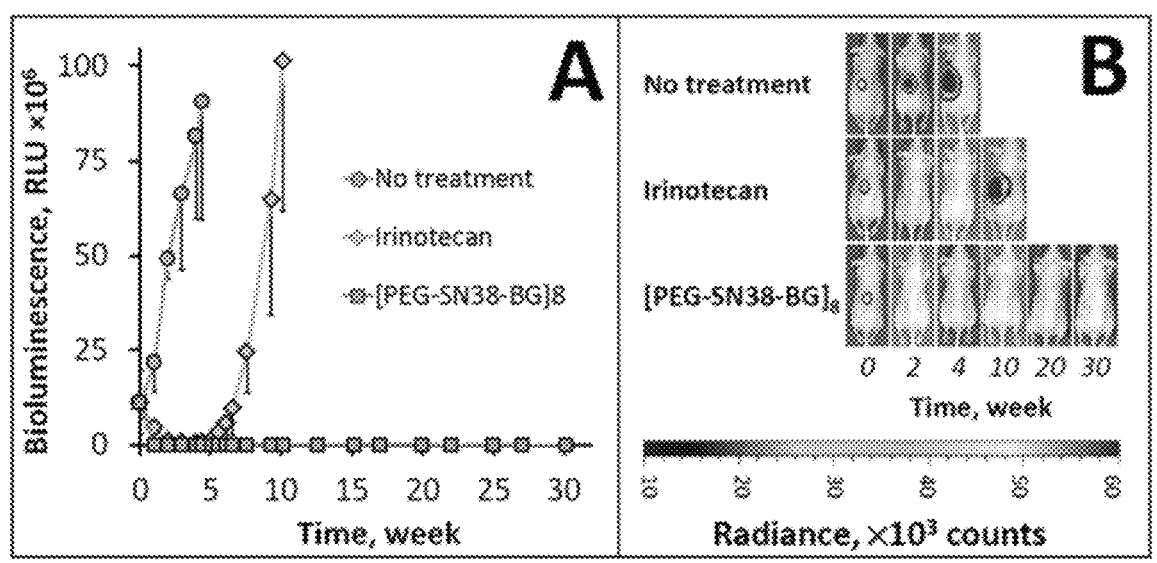
FIG. 17: Therapeutic efficacy of [PEG-SN38-BG]$_8$ in an orthotopic xenograft model of chemo-naïve, MYCN-amplified NB. Mice were inoculated with $10^6$ luciferase-expressing IMR-32 cells. Treatment with the water-soluble precursor of SN-38 (irinotecan) or with [PEG-SN38-BG]$_8$ at doses equivalent to 10 mg SN-38 per kg, 2× week over 4 weeks, was initiated on day 21 after inoculation. Tumor-associated signal was monitored by quantitative bioluminescence. Data in (A) are shown as mean±D. Representative images are included in (B).

When tested in the experimental settings modelling the less therapeutically challenging chemo-naïve disease, irinotecan was able to inhibit tumor growth for the duration of treatment (4 weeks), whereas [PEG-SN38-BG]$_8$ administered over the same time period completely eliminated NB tumors (no detectable regrowth after 30 weeks, FIG. 17). These results provide evidence that NET-targeted delivery with polymeric carrier-linked prodrugs can be optimized to successfully treat different stages (newly diagnosed or relapsed) of aggressive, MYCN-amplified NB.

8. [PEG-SN38-BG]$_8$ Prodrug Causes Regression and Suppresses Regrowth of Disseminated Tumor Deposits in a Model of Metastatic, Drug-Resistant NB.

Figure 18:
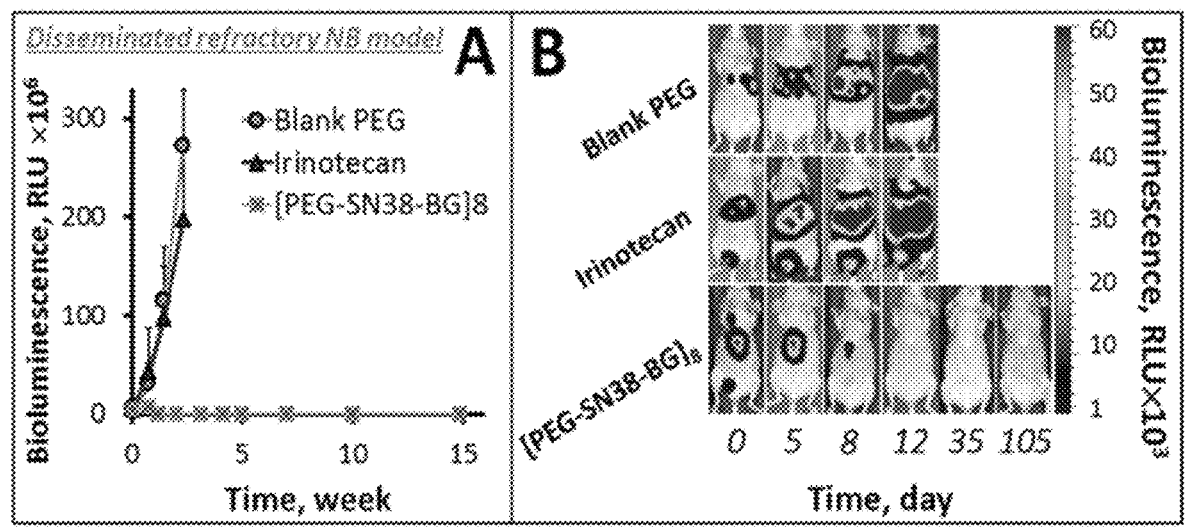
FIG. 18: Therapeutic efficacy of [PEG-SN38-BG]$_8$ in a model of metastatic, refractory NB. Mice were injected through the tail vein with $10^6$ luciferase-expressing BE(2)C cells. Treatment was initiated on day 25 with irinotecan (15 mg/kg) or [PEG-SN38-BG]$_8$ at a dose equivalent to 10 mg SN-38 per kg (4 weeks, 2×/week), Tumor-associated signal was monitored by quantitative bioluminescence ((A), data shown as mean±SD). Representative ages are included is (B).

The effectiveness of tripartite prodrug-based, NET-targeted drug delivery in achieving lasting therapeutic effects against disseminated chemoresistant NB was evaluated in a mouse model of metastatic, refractory disease (FIG. 18). [PEG-SN38-BG]$_8$ administered over 4 weeks caused rapid elimination of established multifocal tumor deposits, with no detectable regrowth over >15 weeks. In contrast, irinotecan given twice a week at a dose of 15 mg/kg had no significant effect on the disease progression (FIG. 18A, B). Taken together with experimentally shown effectiveness of the NET-targeted tripartite prodrug against orthotopic refractory tumors (FIG. 16), these results strongly support the rationale for a prodrug design strategy and its therapeutic potential against both localized and disseminated, high-risk disease not responding to conventional therapy.

9. Prodrug-Mediated Growth Inhibition of MYCN-Amplified, Multidrug-Resistant NB Cells.

Figure 19:
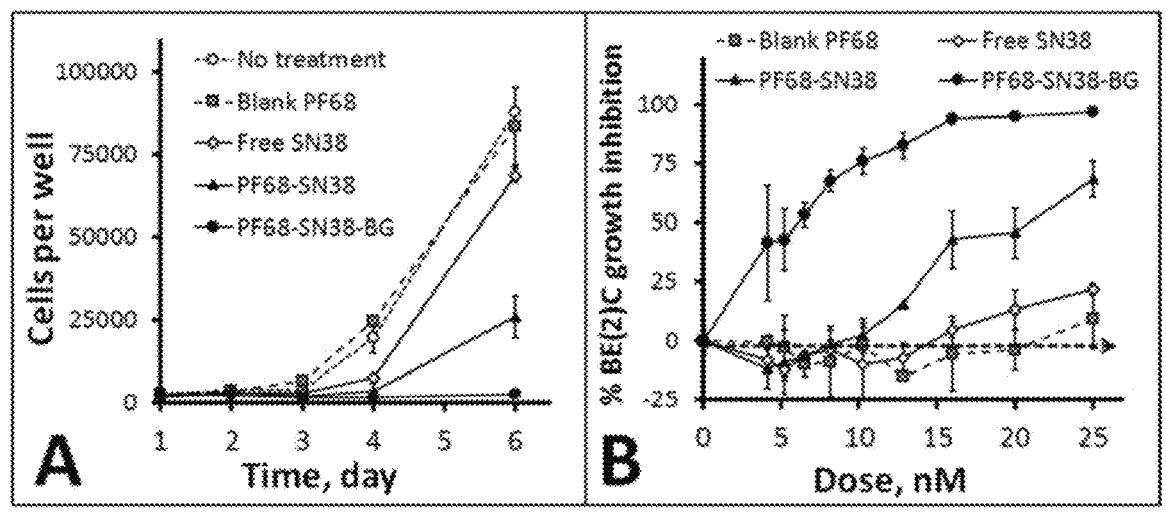
FIG. 19: Antiproliferative effect of PF68-SN38-BG prodrug vs. bipartite (non-targeted) PF68-SN38 and free SN-38 as controls. The response of NB cells exhibiting acquired MDR [BE(2)C] after a 15-min exposure is shown as growth curves (A) and as % growth inhibition (B) at 6 days post treatment as a function of SN-38 equivalent dose (0-25 nM). Cell growth was monitored by bioluminescence. Results are shown as mean±SD.

A strong difference in response patterns was observed when chemoresistant NB cells [BE(2)C] were treated with a NET-targeted tripartite prodrug (PF68-SN38-BG) vs. the non-targeted bipartite control (PF68-SN38) and free SN-38. In agreement with the chemoresistant phenotype of BE(2)C exhibiting a loss of p53 function, BE(2)C cell growth was marginally inhibited by free SN-38. It also exhibited limited and transient response to PF68-SN38. Blank Pluronic F-68 had no effect on cell growth. However, a 15-min exposure to PF68-SN38-BG at doses ≥5 nM of SN-38 resulted in a potent and lasting antiproliferative effect (FIG. 19).

Figure 20:
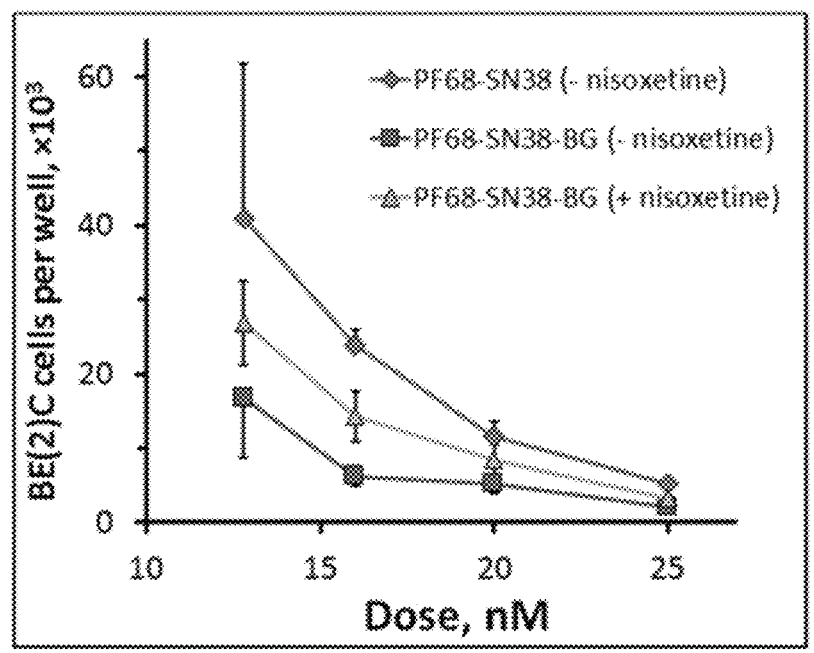
FIG. 20: NET-selectivity of the antiproliferative action of PF68-SN38-BG on chemoresistant NB cells, BE(2)C. Cell growth was examined with/without NET inhibition using nisoxetine (1 μM), in comparison to bipartite PF68-SN38 lacking functionalization with BG (A). Cells were exposed for 15 min to equivalent concentrations of the compounds. Experimental data 6 days post treatment were analyzed by ANOVA with Tukey post-hoc test.

To evaluate the specific contribution of NET affinity built into the prodrug design, the BE(2)C growth inhibitory activity of PF68-SN38-BG was tested with/without a specific NET blocker (nisoxetine, 1 μM). The bipartite PF68-SN38 included as a control showed the lowest growth inhibitory activity at doses ≤20 nM SN-38. The effect of the tripartite PF68-SN38-BG was markedly stronger (P=0.020), yet partially reversible by NET blockade (FIG. 20), confirming the role of NET targeting.

Figure 21:
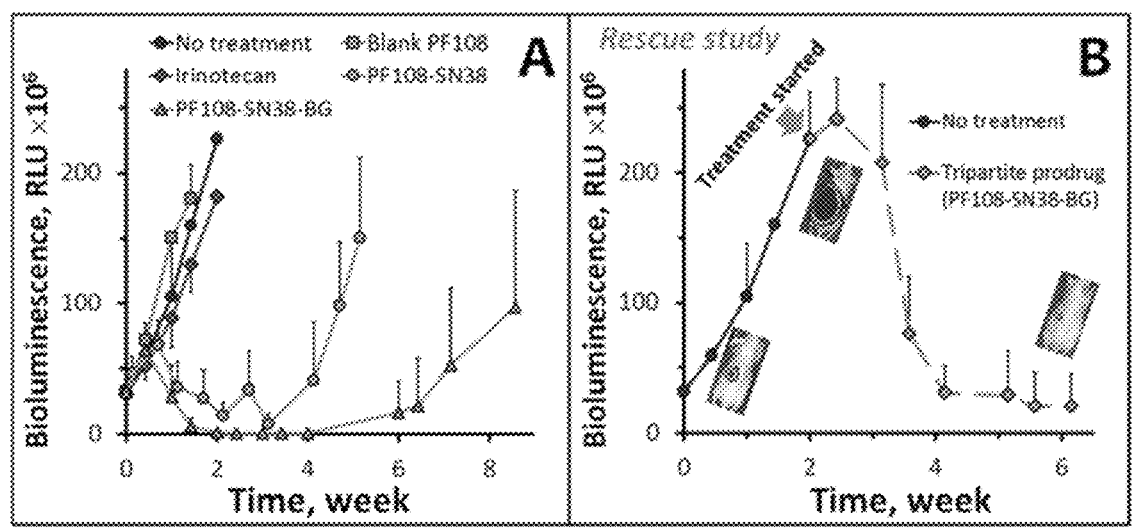
FIG. 21: Therapeutic efficacy of NET-directed delivery in a model of refractory NB. Mice were inoculated in the suprarenal fat pad with $10^6$ luciferase-expressing BE(2)C cells. Treatment was started either with irinotecan (15 mg/kg) or with bipartite and tripartite constructs at a dose equivalent to 10 mg SN-38 per kg (4 weeks, 2×/week, (A)). Alternatively, tumors were allowed to reach 2 cm³ before starting therapy (B). Disease progression was monitored by quantitative bioluminescence. Tumor growth data are shown as mean±SD.

Consistent with these results, a tripartite NET-targeted prodrug synthesized analogously using Pluronic F-108 and administered over 4 weeks (2×/week) caused rapid regression of orthotopic BE(2)C xenograft tumors, in rest to a marginal effect of irinotecan in this model of refractory NB (FIG. 21A 20A). Also unlike bipartite PF108-SN38, the tripartite prodrug stabilized the disease, with no progression during the entire treatment period. Furthermore, animals rapidly approaching the endpoint exhibited remarkable tumor shrinkage when treated with the prodrug ("rescue" study, FIG. 21B).

10. Comparison of PEG-[SN22]4 to PEG-[SN38]4 in an Orthotopic NB Xenograft.

Figure 22:
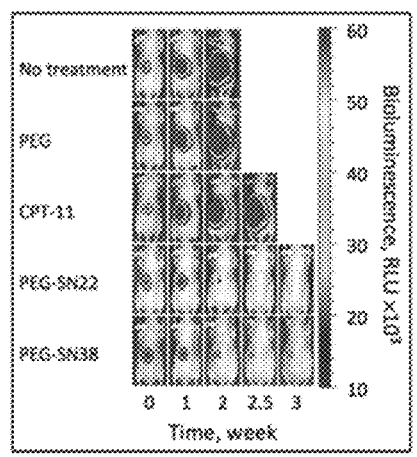
FIG. 22: Chemo-resistant, luciferase-transfected, SKNBE (2)C cells ($10^7$) were injected in the perirenal fat pad of nude mice and followed for tumor development. Mice were divided into five groups: no treatment, or treatment with blank PEG, CPT-11, PEG-[SN22]4 or PEG-[SN38]4 (10 animals per group). Treatment started when tumors reached about 0.2 cm³. Tumor size increased rapidly over 2 weeks in the two control groups, and growth was only slightly delayed by CPT-11. Treatment with either PEG-[SN22]4 or PEG-[SN38]4 slowed growth and then tumors regressed. Only PEG-[SN22]4 treatment caused complete tumor disappearance ((A)=imaging; (B)=quantitation).
Figure 22:
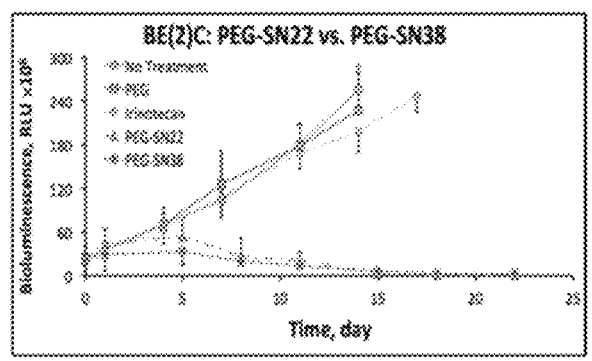

PEG-[SN22]4 was compared to PEG-[SN38]4 in an orthotopic NB xenograft with the chemo-resistant NB line SKNBE(2)C. BE(2)C cells were transfected with a luciferase expression vector to allow for bioluminescent imaging. Mice were treated once week for four weeks with either PEG-[SN22]4 (10 mg/kg/dose), PEG-[SN38]4 (10 mg/kg/dose) or CPT-11 (15 mg/kg/dose), In this chemoresistant model, CPT-11 had very little effect, whereas both PEG-[SN22]4 and PEG-[SN38]4 were extremely effective at shrinking the tumor (FIG. 22). PEG-[SN22]4 treatment resulted in complete disappearance of tumor by 2-3 weeks, but a small tumor remained visible in the PEG-[SN38]4 treated mice. This suggests that PEG-[SN22]4 has superior efficacy in this human NB xenograft mouse model.

Although the invention is illustrated and described herein with reference to specific embodiments, the invention is not intended to be limited to the details described above. Rather, various modifications may be made in the details within the scope and range of equivalents of the claims and without departing from the invention.

The invention claimed is:
1. A macromolecular prodrug which is PEG-[SN22]$_4$, having the following structure:

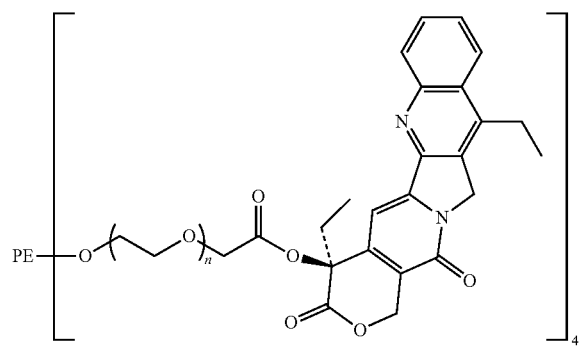

wherein:
n=110 in average and
PE is

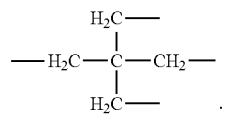

2. A method of treating neuroblastoma, comprising administering an effective amount of the macromolecular prodrug of claim 1 to a subject in need thereof.

3. The method of claim 2, wherein the subject is a human.

4. A method of treating a subject with a solid tumor, comprising administering an effective amount of the macromolecular prodrug of claim 1 to a subject in need thereof.

5. The method of claim 4, wherein the subject is a human.

6. A method of treating a subject with a brain tumor, comprising administering an effective amount of the macromolecular prodrug of claim 1 to a subject in need thereof.

7. The method of claim 6, wherein the subject is a human.

* * * * *